(12) United States Patent
Katayama et al.

(10) Patent No.: US 8,574,150 B2
(45) Date of Patent: Nov. 5, 2013

(54) CAPSULE MEDICAL APPARATUS

(75) Inventors: Miho Katayama, Yokohama (JP);
Shinsuke Tanaka, Hino (JP); Junichi Uchida, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 448 days.

(21) Appl. No.: 12/856,890

(22) Filed: Aug. 16, 2010

(65) Prior Publication Data

US 2011/0166416 A1 Jul. 7, 2011

Related U.S. Application Data

(63) Continuation of application No. PCT/JP2010/052227, filed on Feb. 15, 2010.

(30) Foreign Application Priority Data

Feb. 16, 2009 (JP) .................................. 2009-033112

(51) Int. Cl.
*A61B 1/00* (2006.01)

(52) U.S. Cl.
USPC ........... 600/104; 600/106; 600/121; 600/123; 600/158; 600/170

(58) Field of Classification Search
USPC .................. 600/104, 106, 121, 123, 158, 170
See application file for complete search history.

(56) References Cited

U.S. PATENT DOCUMENTS

| 4,982,739 | A | 1/1991 | Hemstreet et al. | |
|---|---|---|---|---|
| 6,440,147 | B1 | 8/2002 | Lee et al. | |
| 6,776,165 | B2 * | 8/2004 | Jin | ................. 128/899 |
| 8,419,621 | B2 * | 4/2013 | Katayama | ..................... 600/106 |
| 8,480,562 | B2 * | 7/2013 | Katayama | ..................... 600/106 |
| 2005/0272972 | A1 * | 12/2005 | Iddan | ............................ 600/102 |

(Continued)

FOREIGN PATENT DOCUMENTS

| JP | S53-28986 | 3/1978 |
|---|---|---|
| JP | 53-053181 | 5/1978 |

(Continued)

OTHER PUBLICATIONS

Japanese Official Action dated Sep. 21, 2010 together with an English language translation.

(Continued)

*Primary Examiner* — Matthew J Kasztejna
*Assistant Examiner* — Kevin G Barry, III
(74) *Attorney, Agent, or Firm* — Scully, Scott, Murphy & Presser, P.C.

(57) ABSTRACT

A capsule medical apparatus to be introduced into a subject includes a tissue collecting unit that collects in-vivo tissue; a storage unit that stores therein the in-vivo tissue that is collected by the tissue collecting unit; a liquid storing unit that stores therein liquid for suppressing autolysis of in-vivo tissue; a liquid supplying unit that supplies the liquid in the liquid storing unit to the storage unit; and a control unit that allows, in response to an instruction to start collecting the in-vivo tissue, the tissue collecting unit to collect desired in-vivo tissue and to store the collected in-vivo tissue in the storage unit and that then allows the liquid supplying unit to supply the liquid to the storage unit and makes the storage unit be in a liquid-tight state.

12 Claims, 26 Drawing Sheets

(56) References Cited

U.S. PATENT DOCUMENTS

| | | | |
|---|---|---|---|
| 2006/0167339 A1* | 7/2006 | Gilad et al. | 600/106 |
| 2007/0156015 A1* | 7/2007 | Gilad | 600/102 |
| 2007/0213632 A1* | 9/2007 | Okazaki et al. | 600/160 |
| 2008/0199065 A1 | 8/2008 | Swain | |
| 2009/0270681 A1* | 10/2009 | Moreno et al. | 600/155 |

FOREIGN PATENT DOCUMENTS

| | | |
|---|---|---|
| JP | 4-506010 A | 10/1992 |
| JP | 2003-531686 A | 10/2003 |
| JP | 2004-039292 A | 2/2004 |
| JP | 2006-141441 | 6/2006 |
| JP | 2006-239413 A | 9/2006 |
| JP | 2007-181682 A | 7/2007 |
| JP | 2007-537817 A | 12/2007 |
| JP | 2008-500126 | 1/2008 |
| JP | 2008-125643 | 6/2008 |
| WO | WO 2005/113374 | 12/2005 |
| WO | WO 2006/038634 A1 | 4/2006 |

OTHER PUBLICATIONS

Japanese Official Action dated Dec. 14, 2010 together with an English language translation.
Japanese Office Action dated Apr. 5, 2011 issued in JP2010-531365.
International Search Report dated Mar. 9, 2010.

* cited by examiner

BEFORE PUNCTURE NON-RETURN MECHANISM 602 NEEDLE 604 IN-VIVO SURFACE 500

MAGNET 605

1

601 SUCTION DEVICE 603 NEEDLE PROTRUSION/ RETRACTION MECHANISM

DURING PUNCTURE

STORE NEEDLE

CAPSULE MEDICAL APPARATUS

CROSS-REFERENCE TO RELATED APPLICATIONS

This application is a continuation of PCT international application No. PCT/JP2010/052227 filed on Feb. 15, 2010 which designates the United States, incorporated herein by reference, and which claims the benefit of priority from Japanese Patent Applications No. 2009-033112, filed on Feb. 16, 2009, incorporated herein by reference.

BACKGROUND OF THE INVENTION

1. Field of the Invention

The present invention relates to a capsule medical apparatus that is introduced into a subject and that, in the subject, collects and stores in-vivo tissue.

2. Description of the Related Art

In recent years, in the field of endoscopy, capsule-shaped body-insertable apparatuses, for example, capsule endoscopes, that have an imaging function and a wireless communication function have been proposed. A body-insertable apparatus system that acquires images inside a subject using a capsule endoscope has also been developed. To observe and examine inside the subject, from when the capsule endoscope is swallowed, for example, through the mouth of the subject, and until the capsule endoscope is naturally discharged, the capsule endoscope functions so as to move inside a body cavity, for example, inside internal organs, such as the stomach and the small intestine, due to peristaltic movement and capture images inside the subject at, for example, 0.5-second intervals.

While the capsule endoscope moves inside the subject, the images captured by the capsule endoscope are received by an external image display device via an antenna that is arranged on the surface of the subject's body. The image display device has a wireless communication function and an image memory function with respect to the capsule endoscope and sequentially stores, in a memory, the images received from the capsule endoscope inside the subject. Doctors or nurses can observe and examine inside the subject by displaying, on a display, the images, i.e., images of the alimentary canal of the subject, stored in the image display device, thus diagnosing the inside of the subject.

Japanese Patent Application Laid-open No. 2004-39292 discloses a small-sized imaging device that has a sample collecting unit that cuts or scrapes off tissue inside the body cavity of a subject or a specimen and then stores it as a sample.

Furthermore, Japanese Patent Application Laid-open No. 2006-239413 discloses a micromachine that includes an opening/closing mechanism in which a lid member is attached at a suction port or a discharge port of a storage tank and a magnet is attached inside the lid member. By receiving a variable magnetic field from outside and applying resonance or severe vibration to the lid member to destroy the lid member, the opening/closing mechanism releases the suction port or the discharge port. Furthermore, by attaching a non-return valve to the inside or the outside of the lid member, it is possible to prevent the leakage of a substance contained in the storage tank.

SUMMARY OF THE INVENTION

A capsule medical apparatus according to an aspect of the present invention is to be introduced into a subject, and includes a tissue collecting unit that collects in-vivo tissue; a storage unit that stores therein the in-vivo tissue that is collected by the tissue collecting unit; a liquid storing unit that stores therein liquid for suppressing autolysis of in-vivo tissue; a liquid supplying unit that supplies the liquid in the liquid storing unit to the storage unit; and a control unit that allows, in response to an instruction to start collecting the in-vivo tissue, the tissue collecting unit to collect desired in-vivo tissue and to store the collected in-vivo tissue in the storage unit and that then allows the liquid supplying unit to supply the liquid to the storage unit and makes the storage unit be in a liquid-tight state.

A capsule medical apparatus according to still another aspect of the present invention is to be introduced into a subject, and includes a tissue collecting means for collecting in-vivo tissue; a storage means for storing therein the in-vivo tissue that is collected by the tissue collecting means; a liquid storing means for storing liquid that suppresses autolysis of in-vivo tissue; a liquid supplying means for supplying the liquid in the liquid storing means to the storage means; and a control means for allowing, in response to an instruction to start collecting the in-vivo tissue, the tissue collecting means to collect desired in-vivo tissue and to store the collected in-vivo tissue in the storage means and for then allowing the liquid supplying means to supply the liquid to the storage means and making the storing means be in a liquid-tight state.

The above and other features, advantages and technical and industrial significance of this invention will be better understood by reading the following detailed description of presently preferred embodiments of the invention, when considered in connection with the accompanying drawings.

DETAILED DESCRIPTION

In the following, preferred embodiments of a capsule medical apparatus according to the present invention will be described in detail with reference to the accompanying drawings. However, the present invention is not limited to these embodiments.

First Embodiment

Figure 1:
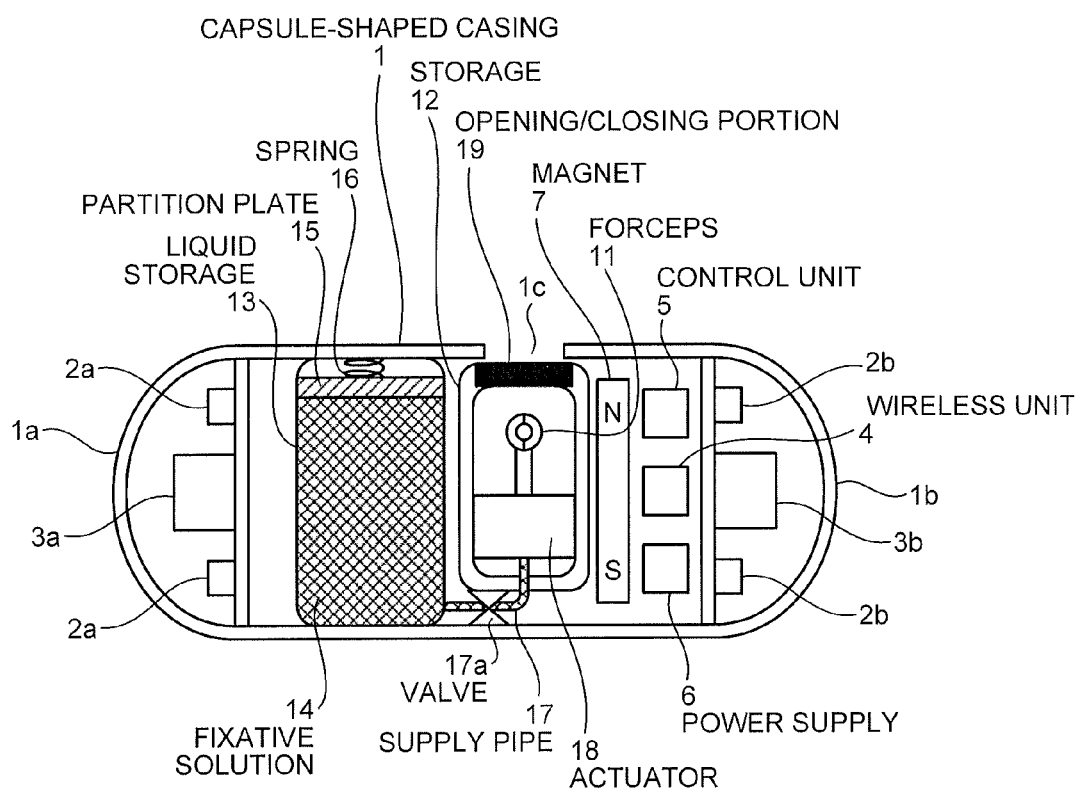
FIG. 1 is a schematic diagram illustrating the configuration of a capsule medical apparatus according to a first embodiment of the present invention.

FIG. 1 is a schematic diagram illustrating the configuration of a capsule medical apparatus according to a first embodiment of the present invention. As illustrated in FIG. 1, the capsule medical apparatus is a capsule-shaped medical apparatus that is formed such that it can be introduced into a subject. The capsule medical apparatus is introduced into the subject; collects in-vivo tissue, such as cells; stores the collected in-vivo tissue; and is discharged outside the subject by storing the collected in-vivo tissue.

With the capsule medical apparatus, openings of a cylindrical casing at both ends are covered by transparent dome-shaped casings 1a and 1b. Various functioning parts are installed in a capsule-shaped casing 1, which functions as an outer casing and has an interior that is maintained in a liquid-tight manner. The capsule medical apparatus includes, near the dome-shaped casings 1a and 1b and on the central axis of the capsule-shaped casing 1, imaging units 3a and 3b that function as an image-capturing means that is implemented by, for example, an image-capturing device and focusing optical system that capture an in-vivo image inside the subject. Furthermore, illumination units 2a and 2b that function as an illumination means that illuminate the inside of the subject and that are implemented by, for example, LEDs are disposed in an annular ring manner in the outer radial direction of the imaging units 3a and 3b.

The capsule-shaped casing 1 includes, in the cylindrical casing thereof, forceps 11 and an actuator 18, functioning as a tissue collecting means or a tissue collecting unit, that collect desired in-vivo tissue. The capsule-shaped casing 1 also includes a storage 12, functioning as a storing space means or a storing unit, that stores therein desired in-vivo tissue that is collected by the forceps 11. Furthermore, the capsule medical apparatus includes a liquid storage 13, functioning as a liquid storing means or a liquid storing unit, that stores therein a fixative solution 14, such as a formalin solution, that suppresses autolysis of the collected in-vivo tissue; a partition plate 15 and a spring 16 that pressurize the fixative solution 14 inside the liquid storage 13; a supply pipe 17 that connects the liquid storage 13 and storage 12; and, in the supply pipe 17, a valve 17a that supplies the fixative solution 14 to the storage 12 or that adjusts the supply amount of the fixative solution 14. Here, the partition plate 15, the spring 16, the supply pipe 17, and the valve 17a correspond to a liquid supplying means or a liquid supplying unit that supplies the fixative solution 14 in the liquid storage 13 to the storage 12.

Furthermore, the capsule-shaped casing 1 includes an opening portion 1c that is used for the forceps 11 to collect in-vivo tissue by protruding/retracting from the casing 1. At the opening portion 1c of the storage 12, the capsule-shaped casing 1 also includes an opening/closing portion 19, functioning as a storage opening/closing means, that can open/close a part of the storage 12. When the opening/closing portion 19 is closed, the storage 12 enters a liquid-tight state. When the opening/closing portion 19 is opened, the forceps 11 collect in-vivo tissue by protruding/retracting through the opening portion 1c.

Furthermore, the capsule medical apparatus includes, inside the capsule-shaped casing 1, a magnet 7, functioning as a magnetic material, that is disposed in such a manner that the magnetization direction corresponds to the radial direction of the capsule-shaped casing 1; a wireless unit 4 that wirelessly transmits, to the outside of the subject, various kinds of information including in-vivo images captured by the imaging units 3a and 3b; a control unit 5, functioning as a control means, that performs a control including controls of processes performed on various components in the capsule-shaped casing 1; and a power supply 6 that supplies, under the control of the control unit 5, electrical power to the various components in the capsule-shaped casing 1.

In the following, a collecting-and-storing process performed on in-vivo tissue using the capsule medical apparatus illustrated in FIG. 1 will be described with reference to FIGS. 2A and 2B. First, the control unit 5 transmits, via the wireless unit 4, in-vivo images that are sequentially captured by the imaging units 3a and 3b to the outside of the subject. An operator determines whether the capsule medical apparatus has reached a position of the in-vivo tissue to be collected by observing, outside the subject, a received in-vivo image. If the capsule medical apparatus reaches the position, the operator performs a collecting process by applying a magnetic field from outside to switch, for example, a magnetic switch (not shown). The capsule medical apparatus can also be forced to move. For example, by generating a rotational magnetic field or a gradient magnetic field from outside, it is possible to allow the capsule medical apparatus to be rotated or linearly moved. Furthermore, the commencement of collecting in-vivo tissue can also be performed by arranging a receiving unit inside the capsule medical apparatus and by wirelessly transmitting a command signal from outside. Alternatively, the commencement of collecting in-vivo tissue can also be performed by arranging, for example, a pH sensor in the capsule medical apparatus or by analyzing an obtained in-vivo image, whereby detecting that the capsule medical apparatus has almost reached the target position inside the subject is performed.

Figure 2A:
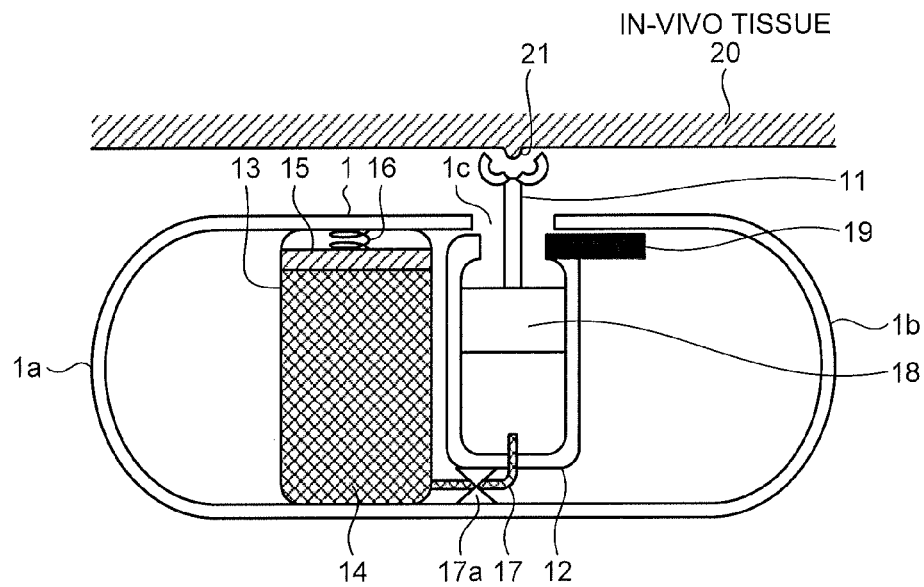
FIG. 2A is a schematic diagram explaining a collecting-and-storing process performed on in-vivo tissue by the capsule medical apparatus illustrated in FIG. 1.
Figure 2B:
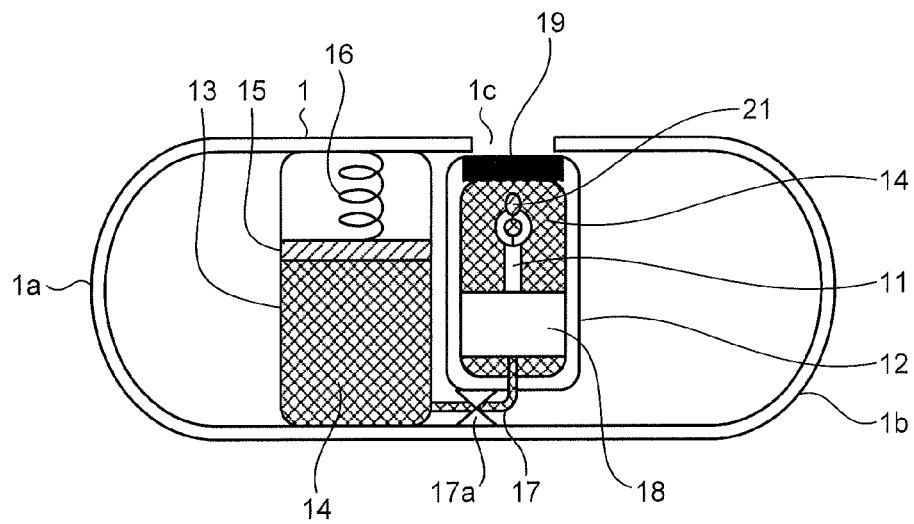
FIG. 2B is another schematic diagram explaining the collecting-and-storing process performed on the in-vivo tissue by the capsule medical apparatus illustrated in FIG. 1.

When the commencement of collecting in-vivo tissue is instructed, the control unit 5 opens, as illustrated in FIG. 2A, the opening/closing portion 19 and operate the actuator 18 so that the forceps 11 protrude on in-vivo tissue 20 side. Then, desired in-vivo tissue 21 is held by the forceps 11 and is stored, together with the forceps 11, in the storage 12. Thereafter, as illustrated in FIG. 2B, after the control unit 5 closes the opening/closing portion 19 and maintains the storage 12 in a liquid-tight manner, the control unit 5 opens the valve 17a and injects, into the storage 12 via the supply pipe 17 using the pressurization applied via the partition plate 15 due to the spring 16, the fixative solution 14 contained in the liquid storage 13 by a predetermined amount or an amount in which the storage 12 is in the full state.

In this way, the fixative solution 14 permeates the in-vivo tissue 21 stored in the storage 12, and, until the capsule medical apparatus is discharged outside the subject and the in-vivo tissue 21 is taken out from the capsule medical apparatus, the in-vivo tissue 21 is maintained in a state in which it is available for pathological examination because autolysis due to catabolic enzymes is suppressed. Furthermore, when the in-vivo tissue 21 is taken out outside the subject, the in-vivo tissue 21 is already in a state in which it is available for pathological examination. Accordingly, an examination, such as tissue processing, can be immediately performed, thus reducing the overall time required for the examination. In addition, when the examination is performed, because the fixative solution 14 maintains the removed in-vivo tissue 21 in a stable manner, the result of the pathological examination is stable.

Figure 3:
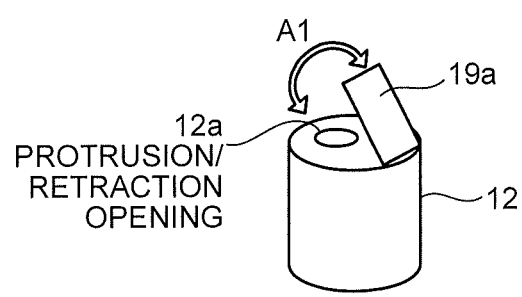
FIG. 3 is a schematic diagram illustrating an example of an opening/closing portion of the capsule medical apparatus illustrated in FIG. 1.
Figure 4:
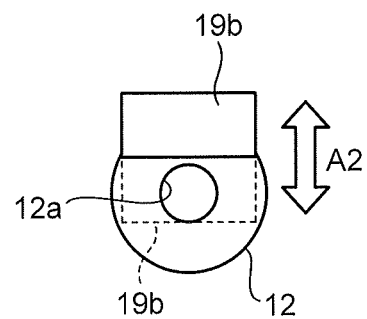
FIG. 4 is a schematic diagram illustrating another example of the opening/closing portion of the capsule medical apparatus illustrated in FIG. 1.
Figure 5:
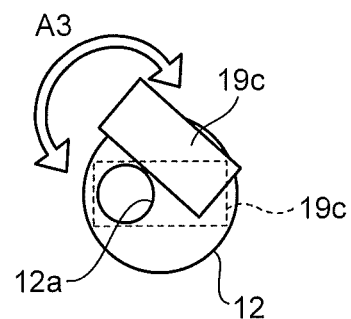
FIG. 5 is a schematic diagram illustrating another example of the opening/closing portion of the capsule medical apparatus illustrated in FIG. 1.

As illustrated in FIG. 3, the opening/closing portion 19 according to the first embodiment described above can be an opening/closing portion 19a that has a cover mechanism like that of a hinged door by arranging a hinge at a predetermined position on a surface around a protrusion/retraction opening 12a of the storage 12 from which the forceps 11 protrude/retract. Furthermore, as illustrated in FIG. 4, the opening/closing portion 19 can be an opening/closing portion 19b that moves in parallel with respect to a surface of an opening of the protrusion/retraction opening 12a. Furthermore, as illustrated in FIG. 5, the opening/closing portion 19 can be an opening/closing portion 19c that rotates in parallel with respect to the surface of an opening of the protrusion/retraction opening 12a. In FIG. 3, the opening/closing direction of the opening/closing portion 19a is indicated by the arrow A1; in FIG. 4, the opening/closing direction of the opening/closing portion 19b is indicated by the arrow A2; and, in FIG. 5, the opening/closing direction of the opening/closing portion 19c is indicated by the arrow A3.

First Modification of First Embodiment

Figure 6:
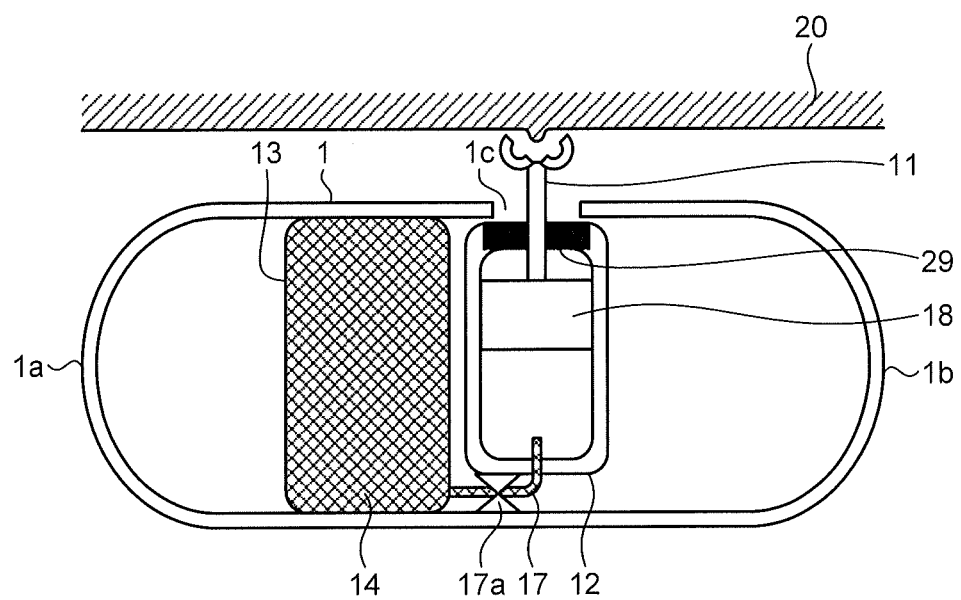
FIG. 6 is a schematic diagram illustrating the configuration of a capsule medical apparatus according to a first modification of the first embodiment of the present invention.

In the following, a first modification of the first embodiment of the present invention will be described. In the first embodiment described above, the forceps 11 can protrude/retract by arranging the opening/closing portion 19 to open/close the opening/closing portion 19. However, in the first modification of the first embodiment, instead of arranging the opening/closing portion 19, as illustrated in FIG. 6, a lid 29 having a non-return function is arranged. The other configurations of the first modification of the first embodiment can be, for example, the same as those in the first embodiment.

The lid 29 is formed of an elastic material, such as rubber, and has a slit at the center through which the forceps 11 can be inserted. Because the lid 29 is formed of an elastic material, a non-return function is implemented in which, when the forceps 11 are not inserted into the slit, the slit is blocked by the elastic force of the elastic material, thereby sealing the storage 12. When the forceps 11 are inserted into the slit, the forceps 11 are brought in close contact with the slit by the elastic force of the elastic material, thereby maintaining the seal.

In the first modification of the first embodiment, the forceps 11 can protrude/retract by maintaining the seal without using a complicated opening/closing mechanism nor a control mechanism, such as the opening/closing portion 19.

Second Modification of First Embodiment

Figure 7A:
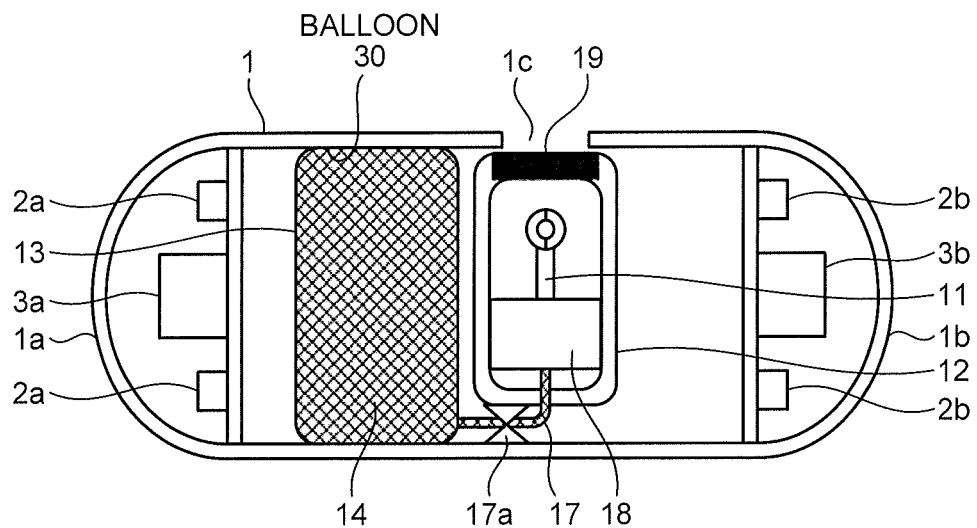
FIG. 7A is a schematic diagram illustrating the configuration of a capsule medical apparatus according to a second modification of the first embodiment of the present invention.

In the following, a second modification of the first embodiment of the present invention will be described. In the first embodiment described above, the fixative solution 14 in the liquid storage 13 is pushed out using the partition plate 15 and the spring 16. However, in the second modification of the first embodiment, as illustrated in FIG. 7A, a balloon 30 is arranged in the liquid storage 13; the balloon 30 is filled with the fixative solution 14; an opening of the balloon 30 is connected to the supply pipe 17; and then the fixative solution 14 in the balloon 30 is pushed out using a contractile force of the balloon 30. The other configurations of the second modification of the first embodiment can be, for example, the same as those in the first embodiment.

Figure 7B:
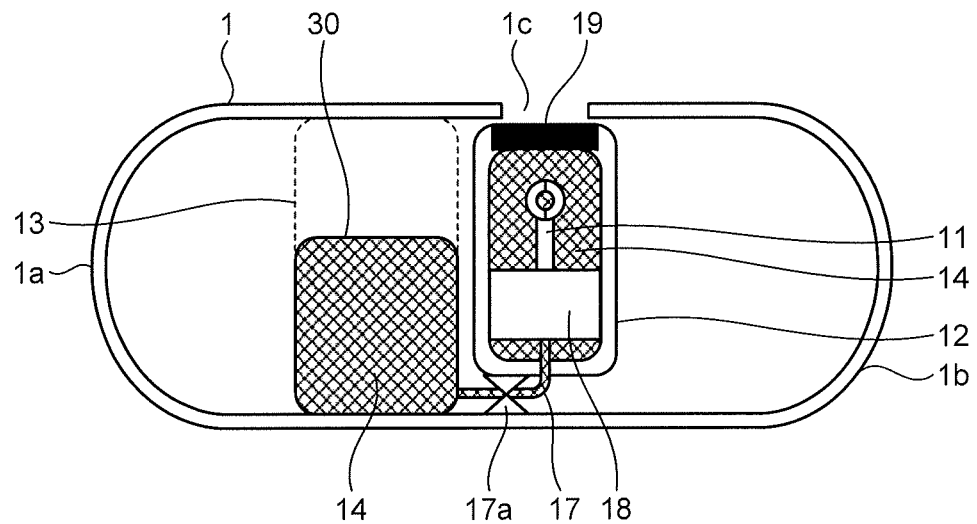
FIG. 7B is a schematic diagram illustrating a state in which, using the capsule medical apparatus illustrated in FIG. 7A, coolant in a liquid storage is pushed out into a storage.

In the second modification of the first embodiment, the balloon 30 is used instead of using the partition plate 15 and the spring 16. Accordingly, as illustrated in FIG. 7B, the configuration for pushing the fixative solution 14 out into the storage 12 can be simple.

Third Modification of First Embodiment

Figure 8:
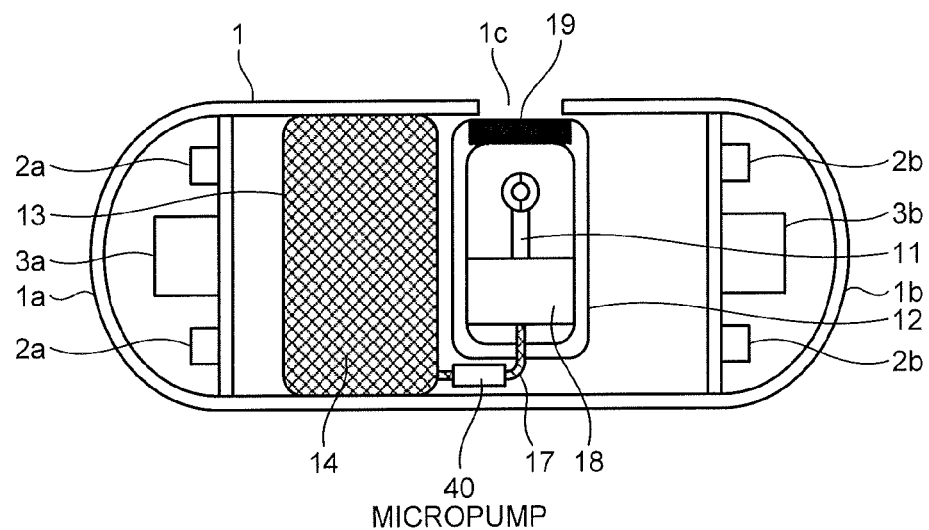
FIG. 8 is a schematic diagram illustrating the configuration of a capsule medical apparatus according to a third modification of the first embodiment of the present invention.

In the following, a third modification of the first embodiment of the present invention will be described. In the first embodiment described above, the operation for injecting the fixative solution 14 into the storage 12 is implemented using the partition plate 15, the spring 16, and the valve 17a. However, in the third modification of the first embodiment, as illustrated in FIG. 8, a micropump 40 supplies the fixative solution 14 to the storage 12. The other configurations of the third modification of the first embodiment can be, for example, the same as those in the first embodiment.

The micropump 40 is preferably small in size and is implemented by using, for example, a micropump that is used when a medical agent is administered. For example, it is preferable to use a peristaltic pump, an osmotic pressure pump, an electro-osmotic pump, or the like. In such a case, when the osmotic pressure pump or the electro-osmotic pump is used, a driving liquid for pushing out the fixative solution 14 is necessary, and the position at which the pump is arranged is upstream in the flow of the fixative solution 14. Furthermore, when a motor driven pump, such as a peristaltic pump, is used, a valve function that restores a decompression state in the liquid storage 13 is preferably arranged at the exterior of the liquid storage 13. Furthermore, the valve function can also be implemented by arranging a film that passes air but that does not pass a liquid.

Fourth Modification of First Embodiment

Figure 9A:
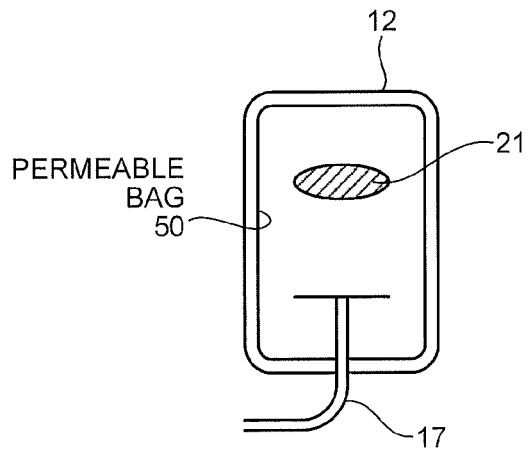
FIG. 9A is a schematic diagram illustrating the configuration of a storage of a capsule medical apparatus according to a fourth modification of the first embodiment of the present invention.

In the following, a fourth modification of the first embodiment of the present invention will be described. In the first embodiment described above, the fixative solution 14 is simply injected into the storage 12. However, in the fourth modification of the first embodiment, as illustrated in FIG. 9A, a permeable bag 50 is arranged in the storage 12 to communicate with the supply pipe 17. The other configurations of the fourth modification of the first embodiment can be, for example, the same as those in the first embodiment.

Figure 9B:
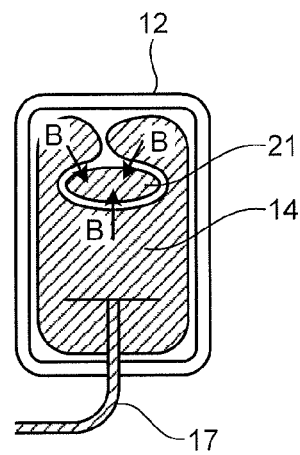
FIG. 9B is a schematic diagram illustrating a state in which, using the capsule medical apparatus illustrated in FIG. 9A, a fixative solution seeps out from a permeable bag.

The permeable bag 50 is formed of a flexible thin film and is formed so as to be porous. As illustrated in FIG. 9B, the permeable bag 50 is formed in such a manner that the fixative solution 14 supplied from the supply pipe 17 to the permeable bag 50 is gradually seeps out. The outer surface thereof is formed of a material to which the collected in-vivo tissue 21 is well adhesive. In FIG. 9B, the directions in which the fixative solution 14 seeps out from the permeable bag 50 is indicated, in outline, by three arrows B. Furthermore, it is preferable to adjust the supply rate or the supply amount of fixative solution 14 from the supply pipe 17 to the permeable bag 50 or to adjust the porous structure of the thin film constituting the permeable bag 50, or alternatively, to adjust both of them in such a manner that the seeping rate of the fixative solution 14 from the permeable bag 50 substantially corresponds to the permeation rate of the fixative solution 14 in the in-vivo tissue 21 permeating into the in-vivo tissue 21. Specifically, the permeable bag 50 can be implemented by a semi-permeable membrane or a film formed of mesoporous silica having a pore diameter of about 2 nm to 10 nm.

In the fourth modification of the first embodiment, because the fixative solution 14 gradually seeps out from the permeable bag 50 into the in-vivo tissue 21, it is possible to further reduce the possibility of the leakage of the fixative solution 14 from the storage 12 to outside.

Fifth Modification of First Embodiment

In the following, a fifth modification of the first embodiment of the present invention will be described. In the first embodiment described above, the opening/closing portion 19 of the storage 12 is arranged at the opening of the capsule-shaped casing 1 from which the forceps 11 protrude/retract. However, in the fifth modification of the first embodiment, the storage 12 is arranged in the capsule-shaped casing 1 by disposing the storage 12 away from the opening of the capsule-shaped casing 1. The other configurations of the fifth modification of the first embodiment can be, for example, the same as those in the first embodiment.

Figure 10A:
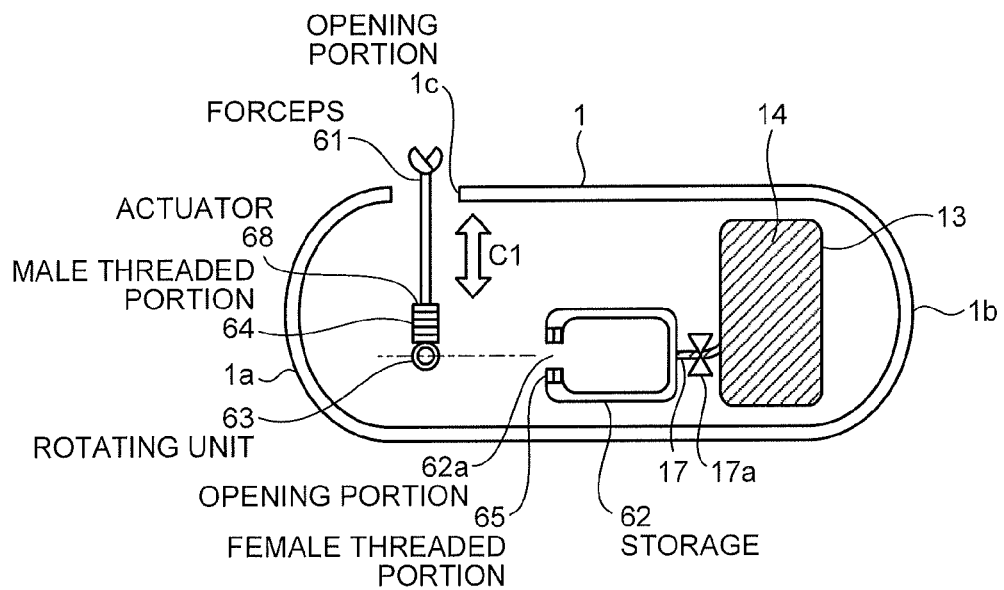
FIG. 10A is a schematic diagram illustrating the configuration and the operation of a capsule medical apparatus according to a fifth modification of the first embodiment of the present invention.
Figure 10B:
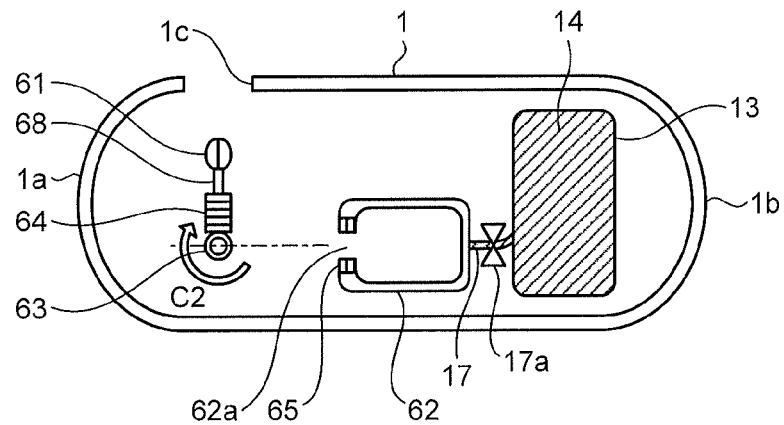
FIG. 10B is another schematic diagram illustrating the configuration and the operation of the capsule medical apparatus according to the fifth modification of the first embodiment of the present invention.
Figure 10C:
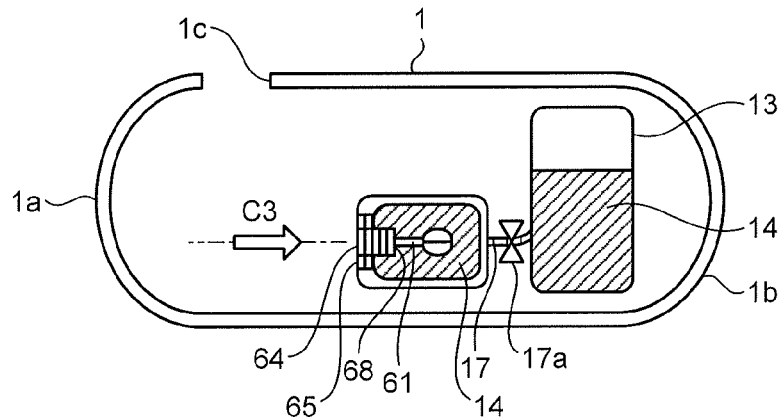
FIG. 10C is another schematic diagram illustrating the configuration and the operation of the capsule medical apparatus according to the fifth modification of the first embodiment of the present invention.

FIGS. 10A, 10B, and 10C are schematic diagrams illustrating the configuration and the operation of a capsule medical apparatus according to the fifth modification of the first embodiment of the present invention. As illustrated in FIGS. 10A to 10C, with the capsule medical apparatus, a storage 62 is arranged at a position away from the opening portion 1c of the capsule-shaped casing 1 from which forceps 61 protrude/retract.

The forceps 61 can expand/contract and rotate about an axis of the forceps 61 using an actuator 68. The forceps 61 can also rotate about a rotating unit 63 functioning as a joint. Furthermore, a male threaded portion 64 is arranged at a proximal end portion of the forceps 61. A female threaded portion 65 is arranged on an internal side surface of an opening portion 62a of the storage 62. The male threaded portion 64 and the female threaded portion 65 can be configured to be engaged with each other. The expansion/contraction direction of the forceps 61 is indicated by the arrow C1 in FIG. 10A; the rotation direction of the forceps 61 is indicated by the arrow C2 in FIG. 10B; and the moving direction of the forceps 61 and the actuator 68 when the male threaded portion 64 is engaged with the female threaded portion 65 is indicated by the arrow C3 in FIG. 10C.

When the capsule medical apparatus collects and stores in-vivo tissue, first, as illustrated in FIG. 10A, the forceps 61 protrude from the capsule-shaped casing 1 through the opening portion 1c to collect in-vivo tissue 21 outside the capsule-shaped casing 1. Then, as illustrated in FIG. 10B, the forceps 61 are contracted while the forceps 61 hold the in-vivo tissue 21 and are rotated about the rotating unit 63 toward the storage 62. Furthermore, as illustrated in FIG. 10C, the forceps 61 are moved toward the opening portion 62a of the storage 62. Then, the forceps 61 are rotated about the axis thereof in a state where the forceps 61 are accommodated in the storage 62, whereby the male threaded portion 64 is engaged with the female threaded portion 65 to make the storage 62 be in a liquid-tight state. Thereafter, by opening the valve 17a, the fixative solution 14 in the liquid storage 13 is supplied to the storage 62 and is made to permeate the in-vivo tissue 21 that is held by the forceps 61.

In the fifth modification of the first embodiment, the storage 62 is arranged at a position away from the opening portion 1c of the capsule-shaped casing 1, and furthermore, the opening portion 62a of the storage 62 does not face the opening portion 1c. Accordingly, it is possible to reduce the possibility of the leakage of the fixative solution 14 contained in the storage 62 from the capsule-shaped casing 1 to the outside.

Sixth Modification of First Embodiment

Figure 11A:
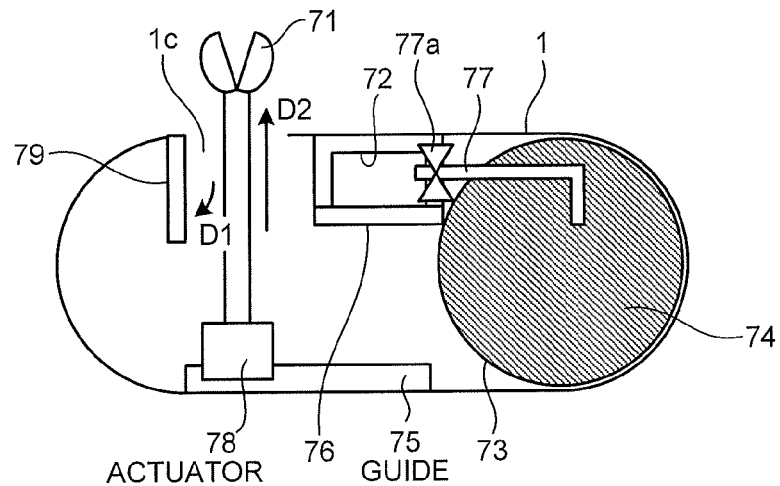
FIG. 11A is a schematic diagram illustrating the configuration and the operation of a capsule medical apparatus according to a sixth modification of the first embodiment of the present invention.
Figure 11B:
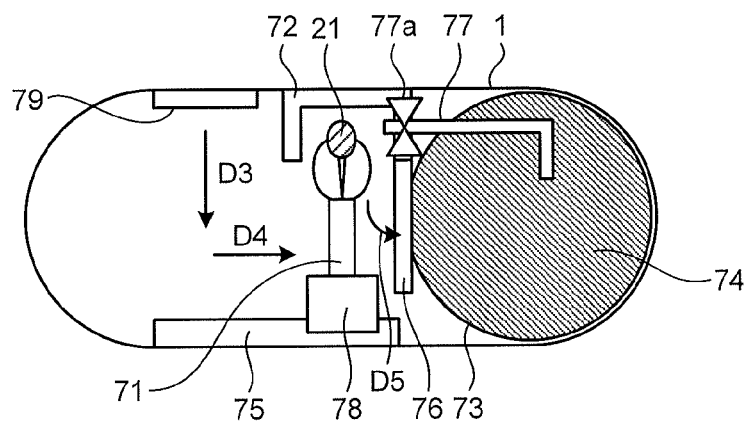
FIG. 11B is another schematic diagram illustrating the configuration and the operation of the capsule medical apparatus according to the sixth modification of the first embodiment of the present invention.
Figure 11C:
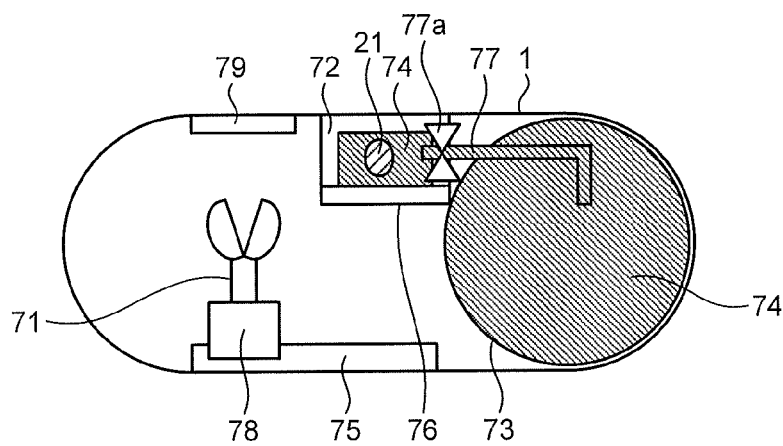
FIG. 11C is another schematic diagram illustrating the configuration and the operation of the capsule medical apparatus according to the sixth modification of the first embodiment of the present invention.

In the following, a sixth modification of the first embodiment of the present invention will be described. In the first embodiment described above, the forceps 11 are accommodated in the storage 12 in a state in which the forceps 11 hold the in-vivo tissue 21. However, in the sixth modification of the first embodiment, as illustrated in FIGS. 11A to 11C, a storage 72 accommodates only the in-vivo tissue 21. The other configurations of the sixth modification of the first embodiment can be, for example, the same as those in the first embodiment.

As illustrated in FIG. 11A, at the opening portion 1c of the capsule-shaped casing 1, the capsule medical apparatus has an opening/closing portion 79, functioning as an outer opening/closing means, that opens/closes the opening portion 1c. Forceps 71 can protrude/retract from the capsule-shaped casing 1 while the opening/closing portion 79 is opened. In FIG. 11A, the displacement direction of the opening/closing portion 79 when the opening portion 1c is opened is indicated by the arrow D1, and the direction of the forceps 71 protruding from the capsule-shaped casing 1 is indicated by the arrow D2. The capsule medical apparatus has a liquid storage 73 that accommodates a fixative solution 74; has the storage 72 to which the fixative solution 74 is supplied via a supply pipe 77 and a valve 77a and which stores therein the in-vivo tissue 21; has an opening/closing portion 76 that opens/closes the storage 72; and has an actuator 78 that protrudes/retracts the forceps 71 from the capsule-shaped casing 1 and that moves the forceps 71 along a guide 75.

As illustrated in FIG. 11A, when the in-vivo tissue 21 is collected by protruding/retracting the forceps 71, the opening/closing portion 76 of the storage 72 is closed. Then, when the forceps 71 hold the in-vivo tissue 21 and are accommodated in the capsule-shaped casing 1, as illustrated in FIG. 11B, the opening/closing portion 79 is closed; the forceps 71 that hold the in-vivo tissue 21 linearly move on the guide 75 together with the actuator 78; and the distal end portion of the forceps 71 are made to face the opening/closing portion 76 of the storage 72. In this state, the opening/closing portion 76 is opened; the forceps 71 are inserted into the storage 72; and the in-vivo tissue 21 is stored in the storage 72 by releasing the held in-vivo tissue 21. In FIG. 11B, the displacement direction when the forceps 71 are accommodated in the capsule-shaped casing 1 is indicated by the arrow D3; the displacement direction when the forceps 71 move together with the actuator 78 toward the storage 72 is indicated by the arrow D4; and the displacement direction of the opening/closing portion 76 when the storage 72 is opened is indicated by the arrow D5. Thereafter, the forceps 71 are moved outside the storage 72 by contracting the forceps 71, and the storage 72 is made to be in the liquid-tight state by closing the opening/closing portion 76. Then, as illustrated in FIG. 11C, the fixative solution 74 is supplied to the storage 72, which is in a liquid-tight state, to allow the fixative solution 74 to permeate the collected in-vivo tissue 21.

In the sixth modification of the first embodiment, because only the in-vivo tissue 21 is stored in the storage 72, a space necessary for the storage 72 can be reduced, thus reducing the size of the storage 72 and also reducing the amount of the fixative solution 74 supplied to the storage 72. Accordingly, the size of the liquid storage 73 can be reduced. As a result, it is possible to reduce the size of the capsule medical apparatus or to implement a multifunctional capsule medical apparatus that has the same volume as a that of the capsule medical apparatus. Furthermore, because the storage 72 is disposed away from the opening portion 1c, it is possible to reduce the possibility of the leakage of the fixative solution 74 in the storage 72 from the capsule medical apparatus.

Seventh Modification of First Embodiment

Figure 12:
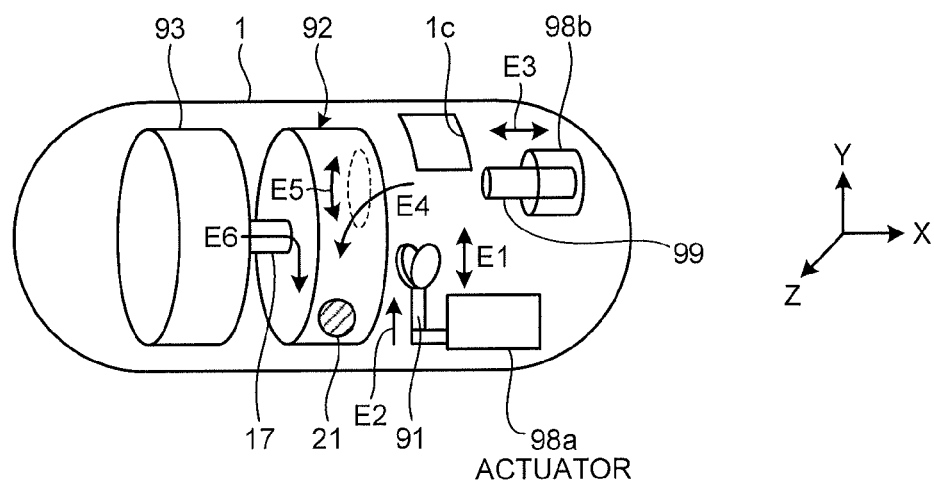
FIG. 12 is a schematic diagram illustrating the configuration of a capsule medical apparatus according to a seventh modification of the first embodiment of the present invention.

In the following, a seventh modification of the first embodiment of the present invention will be described. In the first embodiment described above, the forceps 11 are accommodated in the storage 12 while holding the in-vivo tissue 21. However, in the seventh modification of the first embodiment, as illustrated in FIG. 12, a storage 92 stores therein only the in-vivo tissue 21. The other configurations of the seventh modification of the first embodiment can be, for example, the same as those in the first embodiment.

With the capsule medical apparatus, the opening portion 1c of the capsule-shaped casing 1 and the storage 92 are arranged in a separate manner. Forceps 91 collect the in-vivo tissue 21 by protruding/retracting, using an actuator 98a, from the capsule-shaped casing 1 through the opening portion 1c. Here, the capsule medical apparatus has, at a position facing an opening portion of the storage 92, a removing rod 99 that removes the in-vivo tissue 21 held by the forceps 91 and that guides the in-vivo tissue 21 into the storage 92, and an actuator 98b that expands/contracts the removing rod 99 onto the opening portion side of the storage 92.

The forceps 91 that hold the in-vivo tissue 21 is placed at the front of the storage 92 using the actuator 98a, and, in this state, the actuator 98b protrudes the removing rod 99 onto the storage 92 side, whereby the in-vivo tissue 21 is released from the forceps 91 and is accommodated in the storage 92. Then, the opening portion of the storage 92 is closed; the fixative solution in a liquid storage 93 is supplied to the storage 92; and the fixative solution permeates the in-vivo tissue 21. In FIG. 12, the protrusion/retraction direction of the forceps 91 is indicated by the arrow E1, and the displacement direction of the forceps 91 when the forceps 91 that hold the in-vivo tissue 21 are placed on the front of the storage 92 is indicated by the arrow E2. Furthermore, the expansion/contraction direction of the removing rod 99 is indicated by the arrow E3; the displacement direction of the in-vivo tissue 21 when the in-vivo tissue 21 is accommodated in the storage 92 is indicated by the arrow E4; and the supplying direction of the fixative solution supplied to the storage 92 is indicated by the arrow E5.

In the seventh modification of the first embodiment, because only the in-vivo tissue 21 is stored in the storage 92, the space necessary for the storage 92 can be reduced, thus reducing the size of the storage 92 and also reducing the amount of the fixative solution supplied to the storage 92. Accordingly, the size of the liquid storage 93 can be reduced. As a result, it is possible to reduce the size of the capsule medical apparatus or to implement a multifunctional capsule medical apparatus that has the same volume as that of the capsule medical apparatus. Furthermore, because the storage 92 is disposed away from the opening portion 1c, it is possible to reduce the possibility of the leakage of the fixative solution in the storage 92 from the capsule medical apparatus.

Eighth Modification of First Embodiment

In the following, an eighth modification of the first embodiment of the present invention will be described. In the first embodiment described above, the in-vivo tissue 21 is collected by protruding/retracting the forceps 11. However, in the eighth modification of the first embodiment, instead of the forceps 11, a rotary blade collects the in-vivo tissue 21. The other configurations of the eighth modification of the first embodiment can be, for example, the same as those in the first embodiment.

Figure 13:
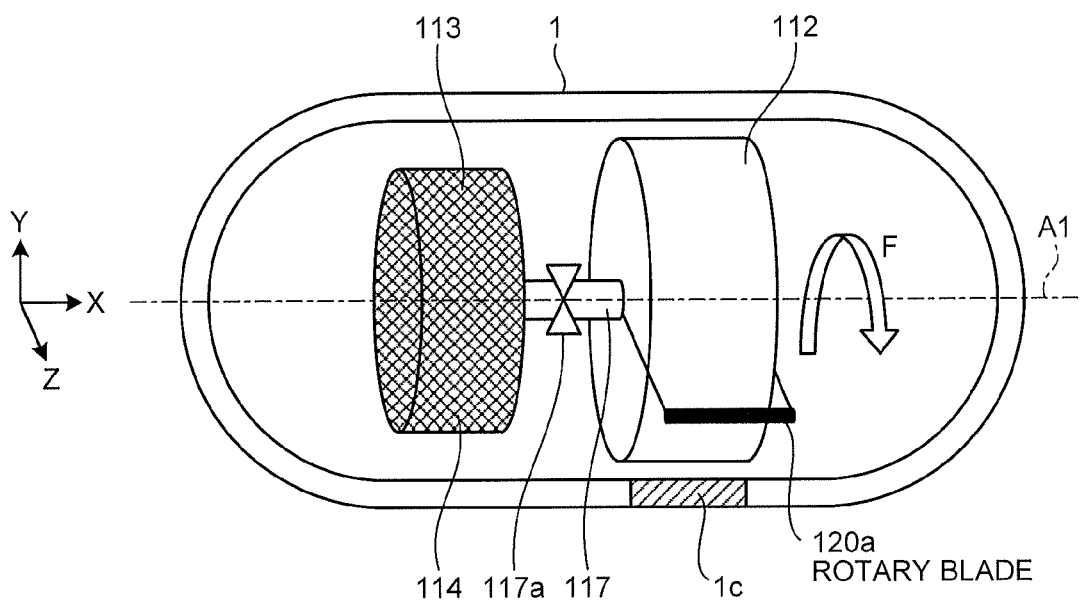
FIG. 13 is a schematic diagram illustrating the configuration of a capsule medical apparatus according to an eighth modification of the first embodiment of the present invention.
Figure 14A:
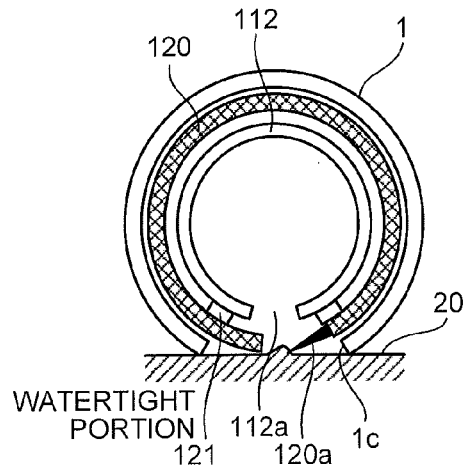
FIG. 14A is a schematic diagram explaining an in-vivo tissue collecting process that uses the rotary blade arranged in the capsule medical apparatus illustrated in FIG. 13.
Figure 14B:
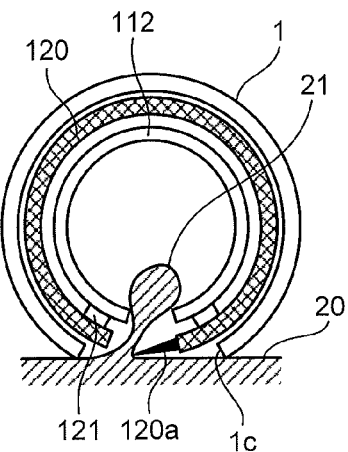
FIG. 14B is another schematic diagram explaining the in-vivo tissue collecting process that uses the rotary blade arranged in the capsule medical apparatus illustrated in FIG. 13.
Figure 14C:
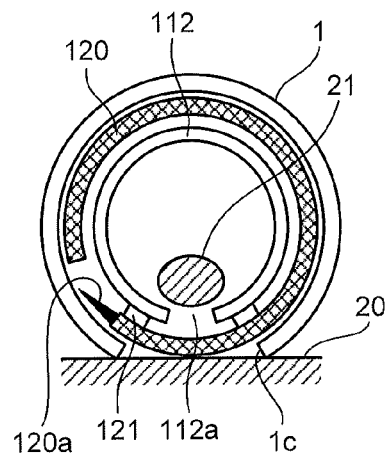
FIG. 14C is another schematic diagram explaining the in-vivo tissue collecting process that uses the rotary blade arranged in the capsule medical apparatus illustrated in FIG. 13.

FIG. 13 is a schematic diagram illustrating the configuration used in the eighth modification of the first embodiment of the present invention. FIGS. 14A to 14C are schematic diagrams explaining an in-vivo tissue collecting process that uses a rotary blade 120a illustrated in FIG. 13. As illustrated in FIGS. 14A to 14C, the capsule medical apparatus has a collecting unit 120 located on a part of the inner circumferential surface of the capsule-shaped casing 1 along in the circumferential direction. As illustrated in FIG. 13 and FIGS. 14A to 14C, the rotary blade 120a that can scrapes off the in-vivo tissue 20 along the circumferential direction is arranged on one end of the collecting unit 120 in the circumferential direction. The rotation direction of the rotary blade 120a is indicated by the arrow F in FIG. 13. Furthermore, the opening portion 1c that is used for the collecting unit 120 to collect the in-vivo tissue 21 is arranged in a part of the capsule-shaped casing 1 in the circumferential direction of the collecting unit 120. Furthermore, a cylindrical storage 112 that stores therein the collected in-vivo tissue 21 is arranged on the inner circumferential of the collecting unit 120. An opening portion 112a that is used to take in the in-vivo tissue 21 is formed on a part of the circumferential direction of the storage 112. Furthermore, a watertight portion 121 is arranged around the opening portion 112a of the storage 112. The opening portion 112a of the storage 112 can be blocked by both the watertight portion 121 and the collecting unit 120 that rotates in the circumferential direction. The storage 112 is connected to a liquid storage 113 via a supply pipe 117 and a valve 117a.

When the in-vivo tissue 21 is collected using the collecting unit 120, first, the opening portion 1c of the capsule-shaped casing 1 abuts against in-vivo tissue to be collected. The opening portion 1c of the capsule-shaped casing 1 and the opening portion 112a of the storage 112 are secured, in an associated manner, at a position in the same circumferential direction. If the collecting unit 120 is rotated about the axis A1 thereof while the opening portion 1c of the capsule-shaped casing 1 abuts against the in-vivo tissue to be collected, as illustrated in FIGS. 14A and 14B, the in-vivo tissue 21 is scraped off by the rotary blade 120a in the collecting unit 120. The scraped in-vivo tissue 21 is stored in the storage 112 via the opening portion 112a of the storage 112 that is arranged in the same circumferential direction of the opening portion 1c of the capsule-shaped casing 1. Then, the collecting unit 120 continues to rotate about the axis A1, and, as illustrated in FIG. 14C, the collecting unit 120 stops its rotation in a state in which the opening portion 112a of the storage 112 is blocked by both the watertight portion 121 and the collecting unit 120, whereby the storage 112 is maintained in a liquid-tight manner. In this state, a fixative solution 114 is supplied to the storage 112 from the liquid storage 113 through both the supply pipe 117 and the valve 117a, and then the fixative solution 114 permeates the in-vivo tissue 21 in the storage 112.

With the eighth modification of the first embodiment, in a similar manner as in the first embodiment, until the in-vivo tissue 21 is taken out from the capsule medical apparatus, it is possible to maintain the in-vivo tissue 21 in a state in which it is available for pathological examination because autolysis due to catabolic enzymes is suppressed.

Second Embodiment

In the following, a second embodiment of the present invention will be described. In the first embodiment described above, a single storage is used for storing in-vivo tissue. However, in the second embodiment, multiple storages are arranged in the capsule-shaped casing 1. The other configurations of the second embodiment can be, for example, the same as those in the first embodiment.

Figure 15:
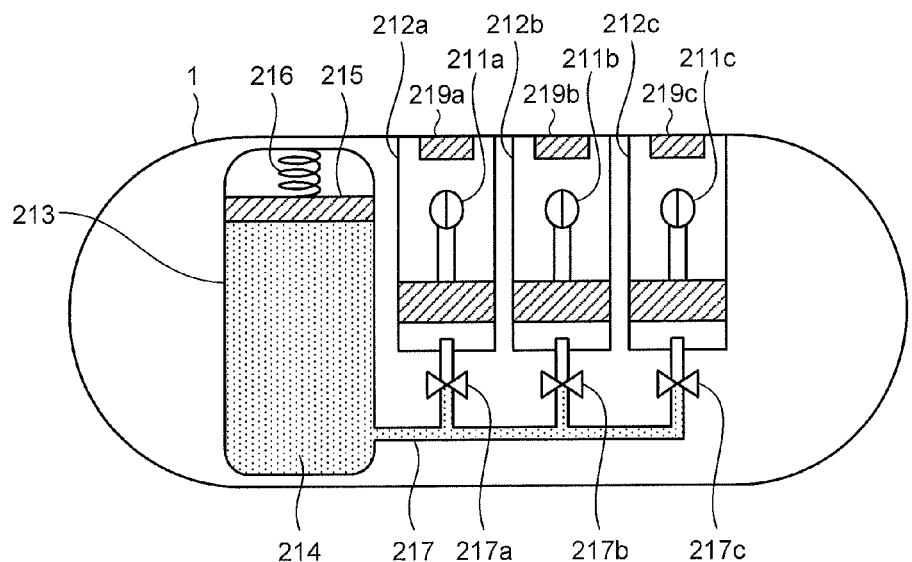
FIG. 15 is a schematic diagram illustrating the configuration of a capsule medical apparatus according to a second embodiment of the present invention.

FIG. 15 is a schematic diagram illustrating the configuration of a capsule medical apparatus according to a second embodiment of the present invention. In FIG. 15, the capsule medical apparatus has a liquid storage 213, a partition plate 215, and a spring 216 that correspond to the liquid storage 13, the partition plate 15, and the spring 16 illustrated in FIG. 1, respectively. Furthermore, the capsule medical apparatus has storages 212a to 212c, forceps 211a to 211c, and opening/closing portions 219a to 219c that correspond to the storage 12, the forceps 11, and the opening/closing portion 19, respectively. Furthermore, the capsule medical apparatus has valves 217a to 217c that correspond to the valve 17a. In other words, the capsule medical apparatus has three storages 212a to 212c that correspond to the storage 12. Here, a supply pipe 217 is branched off from the liquid storage 213 to each of the valves 217a to 217c. Specifically, one single supply pipe 217 connects the liquid storage 213 to each of the storages 212a to 212c.

In the second embodiment, because the multiple storages 212a to 212c and multiple forceps 211a to 211c that are associated with the storages 212a to 212c are arranged, multiple pieces of in-vivo tissue 21 can be separately stored and collected.

First Modification of Second Embodiment

In the following, a first modification of the second embodiment of the present invention will be described. In the second embodiment described above, the forceps 211a to 211c in the storages 212a to 212c each collect the in-vivo tissue 21 and store the in-vivo tissue 21, for each of the forceps, in each of the storages 212a to 212c. However, in the first modification of the second embodiment, only the distal end portion of the forceps that hold the in-vivo tissue 21 is stored in the storage. The other configurations of the first modification of the second embodiment can be, for example, the same as those in the second embodiment.

Figure 16:
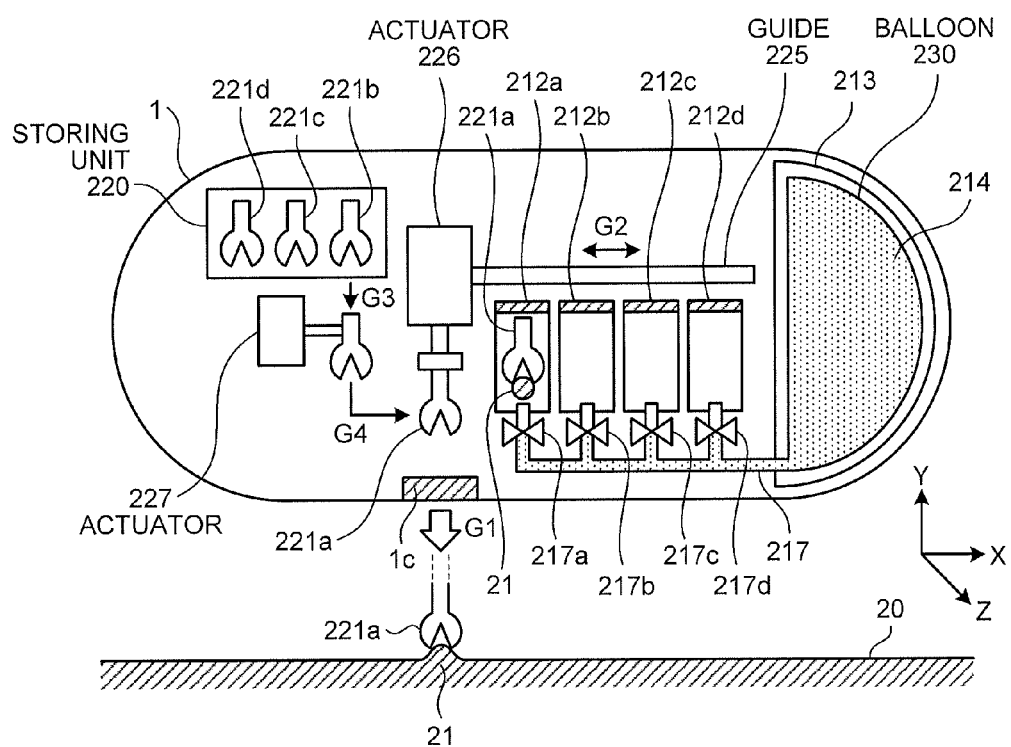
FIG. 16 is a schematic diagram illustrating the configuration of a capsule medical apparatus according to a first modification of the second embodiment of the present invention.

FIG. 16 is a schematic diagram illustrating the configuration of a capsule medical apparatus according to the first modification of the second embodiment of the present invention. In FIG. 16, the capsule medical apparatus has multiple storages 212a to 212d in the capsule-shaped casing 1. A fixative solution 214 in the liquid storage 213 is supplied to the storages 212a to 212d via the valves 217a to 217d. In the first modification of the second embodiment, the fixative solution 214 is forced out from a balloon 230.

The capsule-shaped casing 1 has a single opening portion 1c in order to collect the in-vivo tissue 21. The in-vivo tissue 21 is collected by, using an actuator 226, protruding/retracting the forceps from the opening portion 1c. A distal end portion 221a of the forceps is attached to the distal end portion of the actuator 226. A storing unit 220 stores therein three distal end portions 221b to 221d of forceps, the number of which is obtained by subtracting one from the number of storages 212a to 212d. Furthermore, the distal end portion 221a of the forceps that is used first is attached to the actuator 226.

After the actuator 226 to which the distal end portion 221a of the first forceps is attached collects the in-vivo tissue 21 using the distal end portion 221a of the forceps, the actuator 226 moves along a guide 225 to approach the storage 212a that is used to store the in-vivo tissue 21. Then the actuator 226 removes the distal end portion 221a of the forceps that hold the in-vivo tissue 21 and stores the distal end portion 221a of the forceps in the storage 212a. Thereafter, the valve 217a is opened and the fixative solution 214 is supplied to the storage 212a. In FIG. 16, the protrusion direction of the forceps 221a when the distal end portion 221a of the forceps collects the in-vivo tissue 21 is indicated by the arrow G1, and the moving direction of the actuator 226 along the guide 225 is indicated by the arrow G2.

The actuator 226 stores the distal end portion 221a of the forceps in the storage 212a and then returns to its home position. In this state, an actuator 227 takes out the distal end portion 221b of the next forceps from the storing unit 220 and attaches the distal end portion 221b of the forceps to the distal end of the actuator 226. In FIG. 16, the moving direction of the distal end portion 221b of the next forceps performed by the actuator 227 is indicated by the arrows G3 and G4. Thereafter, the actuator 226 collects the in-vivo tissue 21 by protruding/retracting the distal end portion 221b of the forceps from the opening portion 1c. In a similar manner as in the case in which the in-vivo tissue 21 is collected by the distal end portion 221a of the forceps and is stored, the actuator 226 stores the distal end portion 221b of the forceps that holds the in-vivo tissue 21 in the storage 212b. Then, the fixative solution 214 is supplied to the storage 212b via a valve 217b. Similarly, after the distal end portions 221c and 221d of the forceps collect the in-vivo tissue 21 and the distal end portions 221c and 221d of the forceps are stored in the storages 212c and 212d respectively, the fixative solution 214 is supplied to the storages 212c and 212d.

In the first modification of the second embodiment, because only the distal end portions 221a to 221d of the forceps are stored in the storages 212a to 212d, it is possible to reduce the size of the storage and the amount of the fixative solution 214 to be supplied to each of the storages. Accordingly, the volume of the liquid storage 213 can be reduced, thus further reducing the size of the capsule medical apparatus. Furthermore, the number of actuators to be arranged is not equal to that of the storages, and only the actuator 226 that protrudes/retracts a distal end portion of the forceps and the actuator 227 that takes out the distal end portion of the forceps are required, thus reducing the number of components and facilitating a reduction in size and weight. Furthermore, each of the opening/closing portions of the storage does not need to be arranged near the capsule-shaped casing 1, thus obtaining a flexible design.

Second Modification of Second Embodiment

In the following, a second modification of the second embodiment of the present invention will be described. In the eighth modification of the first embodiment described above, a single storage 112 is arranged, i.e., only a single storing area is arranged. However, in the second modification of the second embodiment, multiple storages are arranged using the configuration of the eighth modification of the first embodiment.

Figure 17:
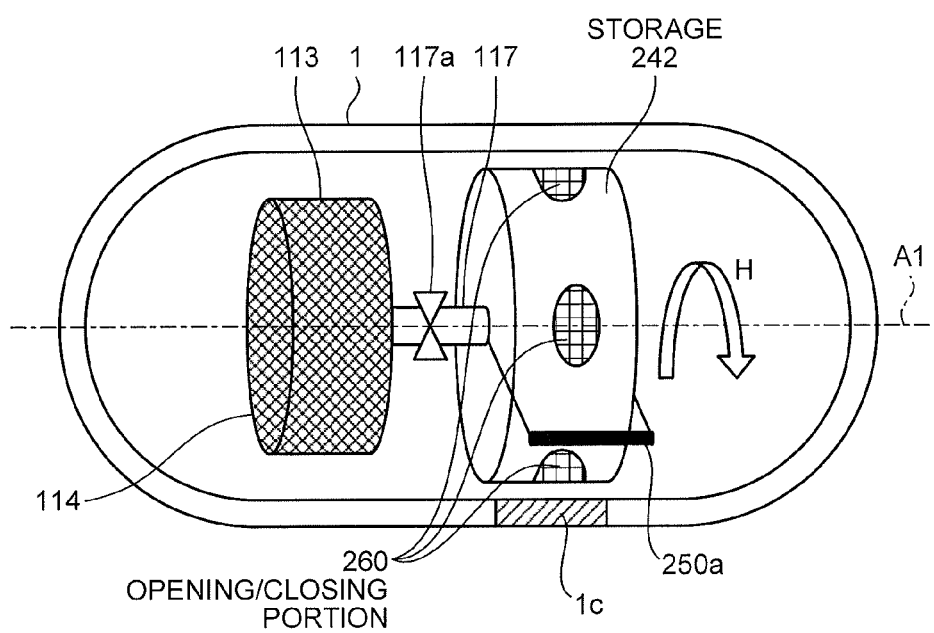
FIG. 17 is a schematic diagram illustrating the configuration of a capsule medical apparatus according to a second modification of the second embodiment of the present invention.
Figure 18A:
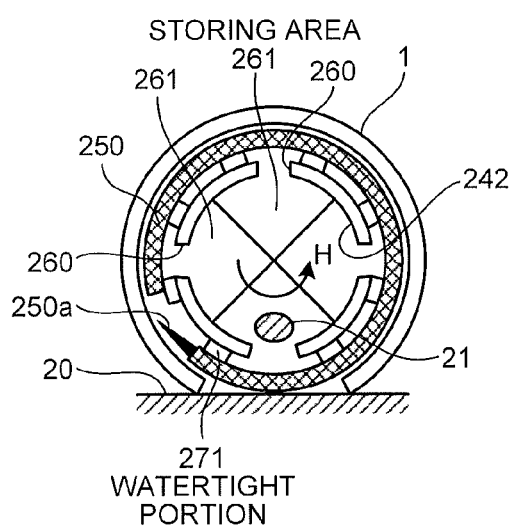
FIG. 18A is a schematic diagram explaining an in-vivo tissue collecting process that uses the rotary blade illustrated in FIG. 17.
Figure 18B:
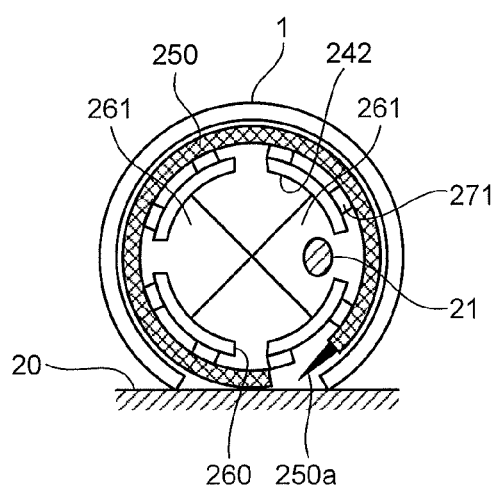
FIG. 18B is another schematic diagram explaining the in-vivo tissue collecting process that uses the rotary blade illustrated in FIG. 17.

FIG. 17 is a schematic diagram illustrating the configuration of a capsule medical apparatus according to a second modification of the second embodiment of the present invention. FIGS. 18A and 18B are schematic diagrams explaining an in-vivo tissue collecting process that uses a rotary blade 250a illustrated in FIG. 17. In FIGS. 17, 18A, and 18B, with the capsule medical apparatus, multiple storing areas 261 having a substantially fan shaped cross section are arranged in a storage 242 around an axis of the capsule-shaped casing 1. In FIGS. 17, 18A, and 18B, four storing areas 261, which are formed at intervals of 90 degrees in the rotation direction of the axis, are formed in the storage 242. Furthermore, opening portions 260 that take in the in-vivo tissue 21 are arranged at the fan-shaped outer circumferential portion in the storing areas 261. Furthermore, watertight portions 271, which are the same as the watertight portion 121 illustrated in FIGS. 14A to 14C, are arranged near the opening portions 260. A collecting unit 250, which corresponds to the collecting unit 120, and the watertight portions 271 block the opening portions 260, whereby each of the storing areas 261 can be maintained in a liquid-tight manner. The collecting unit 250 has a rotary blade 250a in a similar manner as the collecting unit 120.

The operation for collecting the in-vivo tissue 21 performed by the collecting unit 250 and storing the collected in-vivo tissue 21 in each storing area 261 are performed by substantially the same operation as illustrated in FIGS. 14A to 14C. However, as illustrated in FIG. 18B, when the in-vivo tissue 21 has been stored in a single storing area 261, the storage 242 is rotated by 90 degrees, thus enabling the in-vivo tissue 21 to be stored in the neighboring storing area 261. In other words, the storage 242 is configured to be rotatable. The rotation direction of the storage 242 is indicated by the arrow H in FIGS. 17 and 18. At this time, by saving, in the control unit 5, information about a location where the in-vivo tissue 21 is collected and information about which storing areas 261 store the in-vivo tissue 21, it is possible to find out, after the capsule medical apparatus is discharged, the location where each of multiple pieces of in-vivo tissue 21 were collected.

In the second modification of the second embodiment, also for the capsule medical apparatus having the configuration described in the eighth modification of the first embodiment, it is possible to arrange multiple storing regions using substantially the same configuration, and, even when multiple pieces of in-vivo tissue are collected and stored, it is also possible to reduce the size of the capsule medical apparatus.

Third Modification of Second Embodiment

In the following, a third modification of the second embodiment of the present invention will be described. In the seventh modification of the first embodiment described above, a single piece of in-vivo tissue 21 is stored in the storage 92. However, in the third modification of the second embodiment, multiple pieces of in-vivo tissue 21 can be collected and stored even when the configuration described in the seventh modification of the first embodiment is used.

Figure 19:
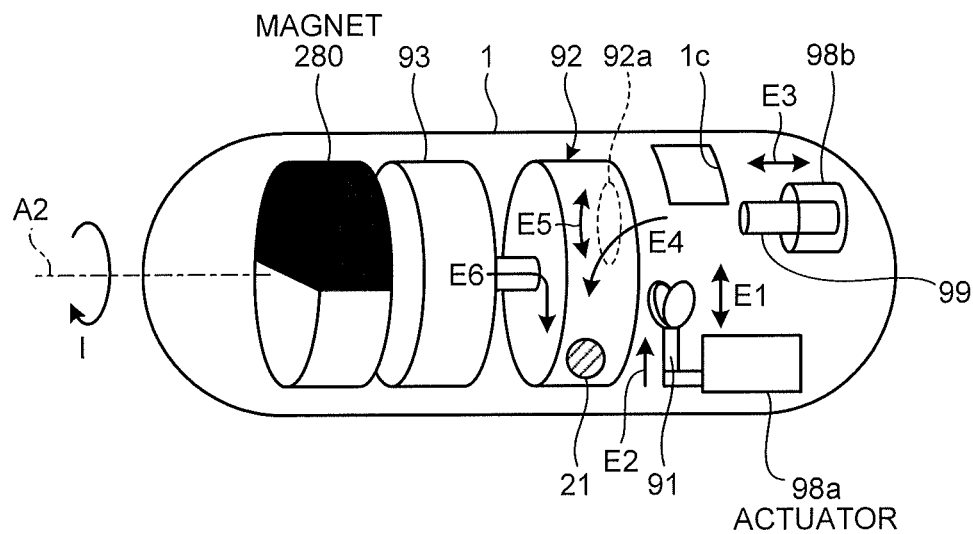
FIG. 19 is a schematic diagram illustrating the configuration of a capsule medical apparatus according to a third modification of the second embodiment of the present invention.

Specifically, as illustrated in FIG. 19, a magnet 280 functioning as a magnetic material is arranged in the capsule-shaped casing 1, and an external magnetic field rotates the capsule-shaped casing 1 and changes the orientation thereof. The magnet 280 is arranged such that, for example, the magnetization direction corresponds to the radial direction of the capsule-shaped casing 1. The process for collecting and saving the first in-vivo tissue 21 is the same as that performed in the seventh modification of the first embodiment. However, when the next in-vivo tissue 21 is collected using the forceps 91, to position an opening portion 92a of the storage 92 on the upper side in the gravity direction, the capsule medical apparatus is rotated about the axis A2 thereof by generating a rotating field from outside or the capsule medical apparatus is moved linearly by generating a magnetic attracting force. By doing so, because the fixative solution supplied to the storage 92 moves toward the lower side in the direction in which gravity acts, the fixative solution does not leak when the in-vivo tissue 21 is taken in the storage 92 by opening the opening portion 92a. In other words, multiple pieces of in-vivo tissue 21 can be stored without the fixative solution leaking. In FIG. 19, the rotation direction of the capsule medical apparatus is indicated by the arrow I.

The storage 92 is not preferably fully filled with the fixative solution; the amount of fixative solution supplied to the storage 92 is preferably a level in which the solution surface is lower than the opening portion 92a when the opening portion 92a is positioned on the upper side relative to the direction in which gravity acts. Furthermore, in such a case, after the in-vivo tissue 21 is collected and stored, by rotating the capsule medical apparatus using the above described external magnetic field, it is preferable to make a state in which the fixative solution always permeates the in-vivo tissue 21 in the storage 92. Furthermore, if it is possible to collect the in-vivo tissue 21 and to rotate after the in-vivo tissue 21 is stored in this way, the amount of fixative solution to be supplied to the storage 92 is small. In such a case, the volume of the liquid storage 93 that stores the fixative solution can be reduced, facilitating a size reduction.

Third Embodiment

In the following, a third embodiment of the present invention will be described. In both the first and second embodiments described above, autolysis of the in-vivo tissue in the storage is reduced by supplying the fixative solution, such as a formalin solution, to the storage. In the third embodiment, autolysis of in-vivo tissue is suppressed by cooling the in-vivo tissue. The other configurations of the third embodiment can be, for example, the same as those in the first and second embodiments.

Figure 20:
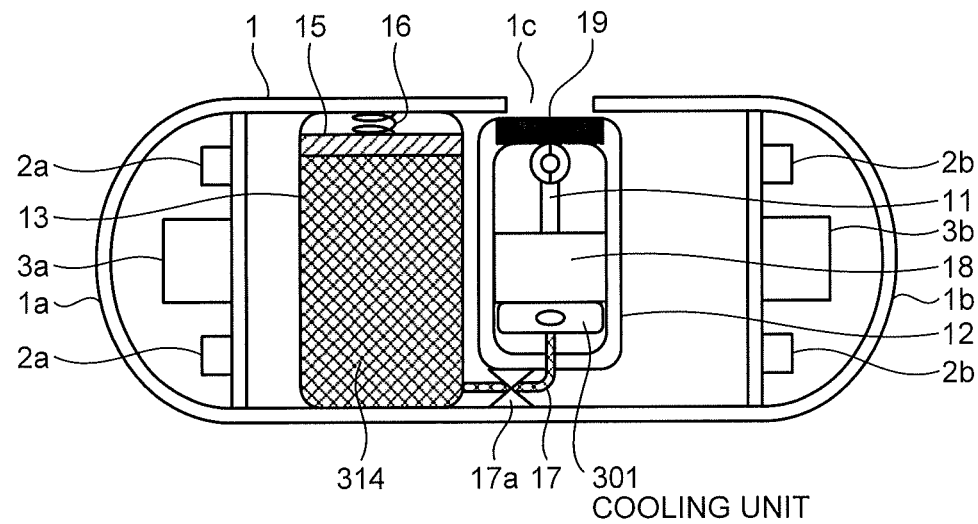
FIG. 20 is a schematic diagram illustrating the configuration of a capsule medical apparatus according to a third embodiment of the present invention.
Figure 21A:
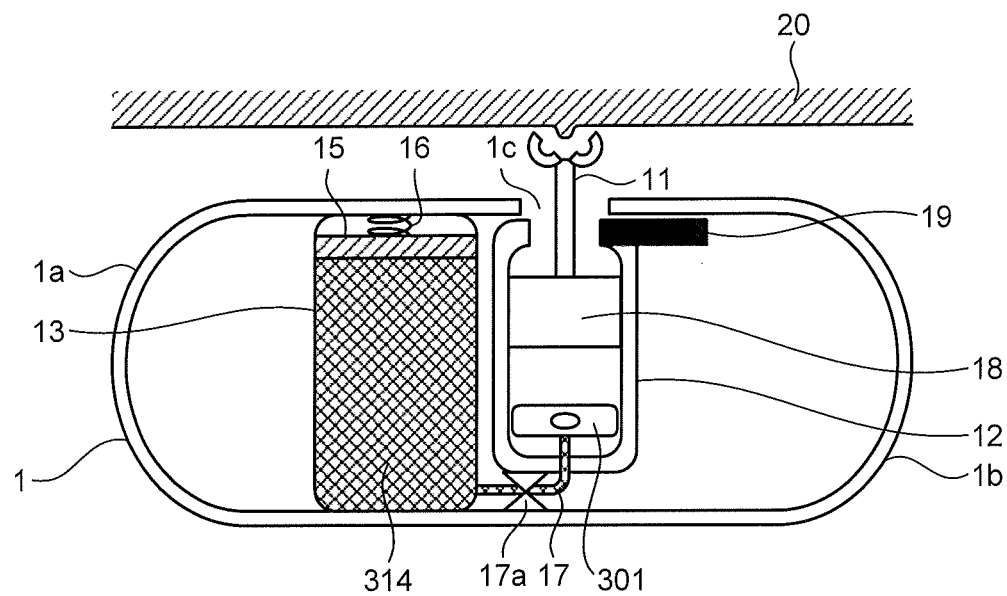
FIG. 21A is a schematic diagram explaining a collecting-and-storing process performed on in-vivo tissue by the capsule medical apparatus according to the third embodiment of the present invention.
Figure 21B:
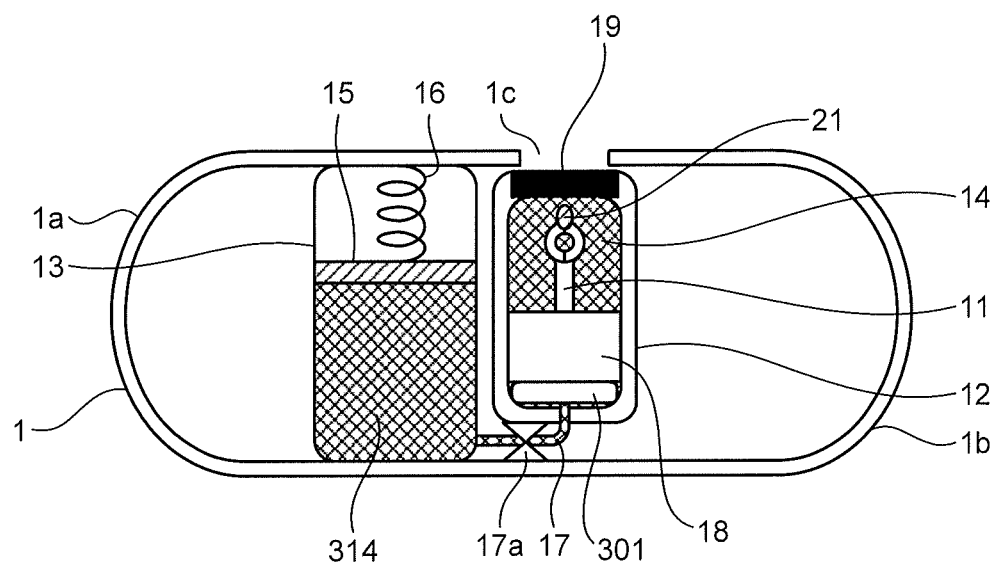
FIG. 21B is another schematic diagram explaining the collecting-and-storing process performed on in-vivo tissue by the capsule medical apparatus according to the third embodiment of the present invention.

FIG. 20 is a schematic diagram illustrating the configuration of a capsule medical apparatus according to a third embodiment of the present invention. FIGS. 21A and 21B are schematic diagrams explaining a collecting-and-storing process performed on in-vivo tissue by the capsule medical apparatus according to the third embodiment of the present invention. As illustrated in FIGS. 20, 21A, and 21B, in capsule medical apparatus, the in-vivo tissue 21 that is collected and then stored in the storage 12 is cooled in such a manner that the in-vivo tissue 21 is not frozen This is achieved by arranging a cooling unit 301 in the storage 12; by cooling the storage 12 after the in-vivo tissue 21 is stored in the storage 12; and by supplying, to the storage 12, an antifreeze solution 314, such as ethanol, that is stored in the liquid storage 13. Because the in-vivo tissue 21 is cooled, the generation and action of catabolic enzymes are suppressed and thus autolysis is suppressed. The other configurations of the third embodiment can be the same as those in the first embodiment illustrated in FIG. 1. Components that are identical to those in the first embodiment are assigned the same reference numerals.

The cooling unit 301 includes, for example, powder ammonium sulfate and a pack of water. With the capsule medical apparatus, first, as illustrated in FIG. 21A, the forceps 11 collect the in-vivo tissue 21. After the in-vivo tissue 21 is collected, the actuator 18 is lowered; the pack that contains the water in the cooling unit 301 is broken due to the lowering of the actuator 18; the ammonium sulfate is mixed with the water to generate a cooling action due to the heat of solution; and then the storage 12 is cooled. In this state, as illustrated in FIG. 21B, the antifreeze solution 314 is supplied to the storage 13 from the liquid storage 13, thus preventing the in-vivo tissue 21 from freezing.

As a result, until the in-vivo tissue 21 is taken out from the capsule medical apparatus, the autolysis due to the catabolic enzymes is suppressed in the in-vivo tissue 21, thus maintaining a state in which the in-vivo tissue 21 is available for pathological examination. Furthermore, when the in-vivo tissue 21 is taken out outside the subject, the in-vivo tissue 21 is already in a state in which it is available for pathological examination. Accordingly, an examination, such as tissue processing, can be immediately performed, thus reducing the overall time required for the examination.

Furthermore, instead of the ammonium sulfate, for example, ammonium nitrate, ammonium chloride, or sodium carbonate can be used in the cooling unit 301. Furthermore, the cooling unit 301 can have a cooling function.

Furthermore, in the third embodiment described above, using the cooling unit 301 and the antifreeze solution 314, the in-vivo tissue 21 is cooled in such a manner that it is not frozen; however, the configuration is not limited thereto. For example, a liquefied refrigerant can be stored in the liquid storage 13, and the in-vivo tissue 21 can be cooled by filling the storage 12 with the refrigerant or vaporized refrigerant. In this case, it is preferable not to freeze the in-vivo tissue 21. Accordingly, it is preferable to control the temperature in the storage 12 by arranging, for example, a temperature sensor that detects the temperature of the storage 12.

First Modification of Third Embodiment

Figure 22:
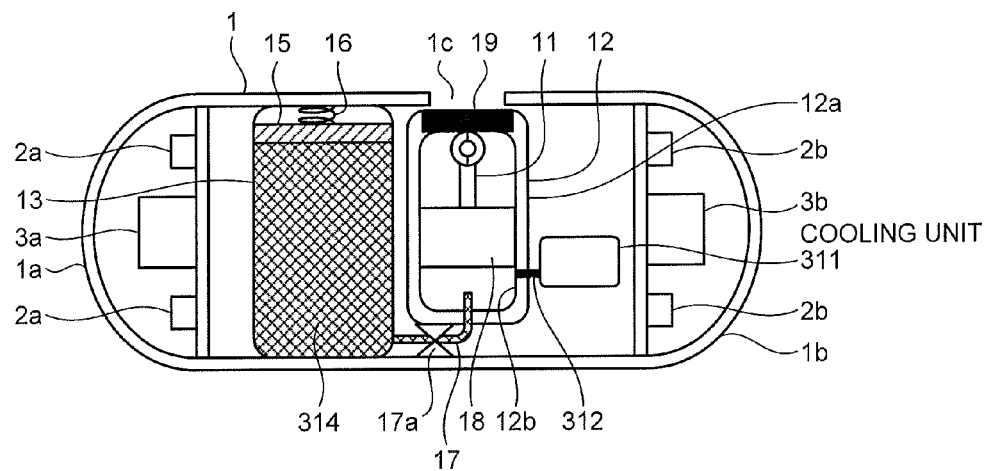
FIG. 22 is a schematic diagram illustrating the configuration of a capsule medical apparatus according to a first modification of the third embodiment of the present invention.

In the following, a first modification of the third embodiment of the present invention will be described. In the third embodiment, the cooling unit 301 is arranged in the storage 12. However, in the first modification of the third embodiment, as illustrated in FIG. 22, a cooling unit 311 is arranged outside the storage 12, and the cooling unit 311 and the storage 12 are connected using a heat transferring unit 312, thus cooling the inside of the storage 12. The other configurations of the first modification of the third embodiment can be, for example, the same as those in the third embodiment.

Here, the storage 12 has a double layered casing; an external layer 12a is formed of a heat blocking member that blocks heat conduction; and an internal layer 12b is formed of a high heat conducting material. With this configuration, the endothermic load on the cooling unit 311 from the storage 12 can be reduced, thus implementing a size reduction of the cooling unit 311 and maintaining the cooling of the storage 12. In this case, in a similar manner as in the third embodiment, the antifreeze solution 314 is preferably supplied to the storage.

Second Modification of Third Embodiment

Figure 23:
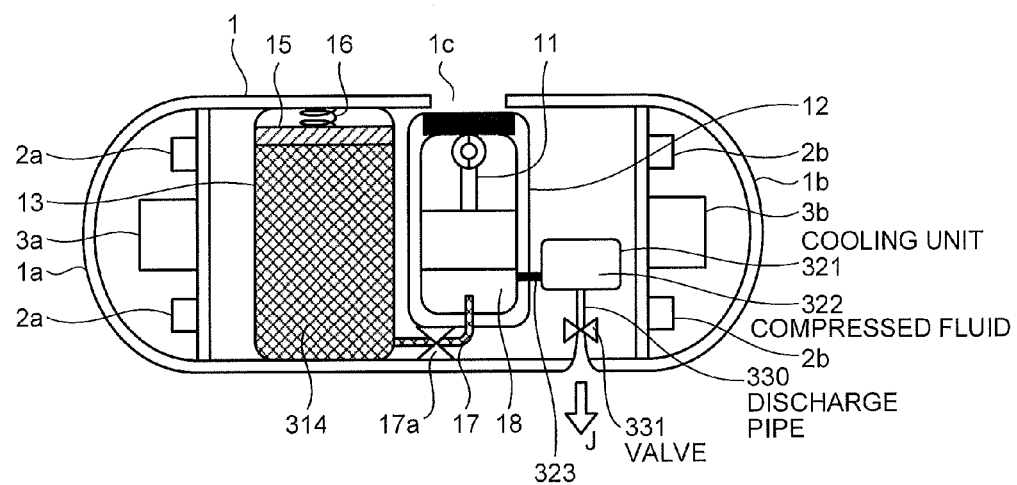
FIG. 23 is a schematic diagram illustrating the configuration of a capsule medical apparatus according to a second modification of the third embodiment of the present invention.

In the following, a second modification of the third embodiment of the present invention will be described. In the third embodiment described above, the cooling unit 301 is arranged in the storage 12. However, in the second modification of the third embodiment, as illustrated in FIG. 23, a cooling unit 321 that cools the storage 12 using vaporization heat obtained when a compressed fluid 322 is vaporized is arranged outside the storage 12, and the cooling unit 321 and the storage 12 are connected by a heat transferring unit 323. The other configurations of the second modification of the third embodiment can be, for example, the same as those in the third embodiment.

In the second modification of the third embodiment, in a similar manner as in the first modification of the third embodiment, the cooling unit 321 is arranged outside the storage 12. When the compressed fluid 322 stored in the cooling unit 321 is discharged from a discharge pipe 330 to the outside of the capsule-shaped casing, the cooling unit 321 cools the storage 12 using a property in which the compressed fluid 322 is vaporized by removing heat from the surroundings. In other words, the cooling unit 321 cools using the vaporization heat of the compressed fluid 322. In FIG. 23, the discharging direction of the compressed fluid 322 is indicated by the arrow J. The cooling capacity of the compressed fluid 322 is controlled by adjusting the degree of opening of a valve 331 arranged in the discharge pipe 330. Furthermore, the storage 12 preferably has a double layer in a similar manner as in the first modification of the third embodiment.

Fourth Embodiment

In the following, a fourth embodiment of the present invention will be described. In the fourth embodiment, absorbers that absorb a solution are arranged so as to cover components from which the fixative solution is possibly leaked, such as the storage of the capsule medical apparatus, the liquid storage, the supply pipe that connects the storage to the liquid storage, and the valve. The other configurations of the fourth embodiment can be, for example, the same as those in the first to third embodiments.

Figure 24:
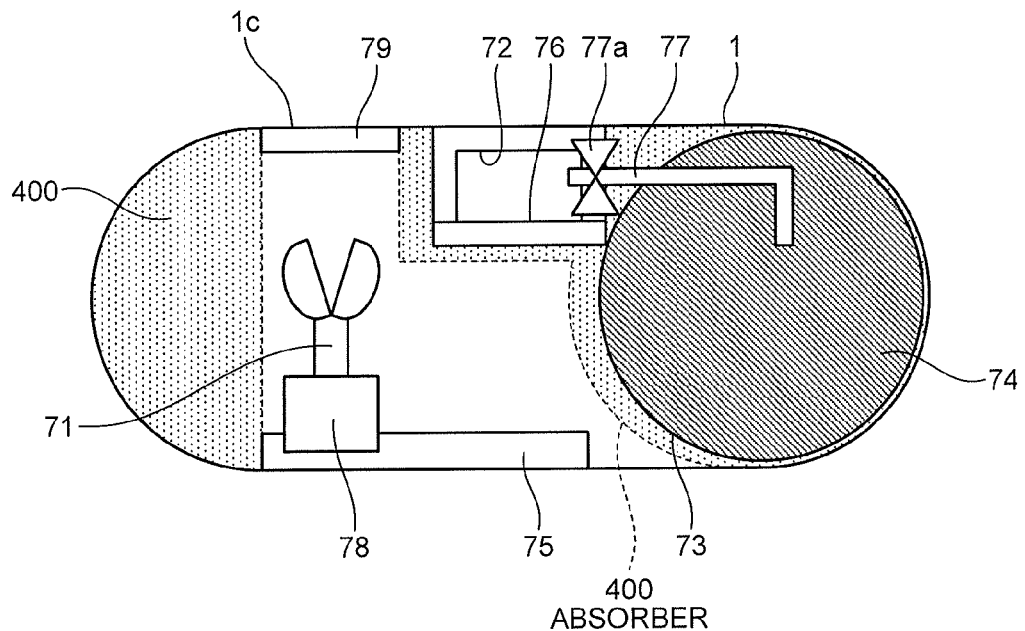
FIG. 24 is a schematic diagram illustrating the configuration of a capsule medical apparatus according to a fourth embodiment of the present invention.

FIG. 24 is a schematic diagram illustrating the configuration of a capsule medical apparatus according to the fourth embodiment of the present invention. The capsule medical apparatus corresponds to the capsule medical apparatus of the sixth modification of the first embodiment illustrated in FIGS.

11A to 11C. Absorbers 400 are arranged so as to cover at least the storage 72, the valve 77a, the supply pipe 77, and the liquid storage 73.

By arranging the absorbers 400 in this way, even when the fixative solution 74 is leaked, because the absorbers 400 absorb the fixative solution 74, it is possible to prevent the fixative solution 74 from leaking outside of the capsule-shaped casing 1.

First Modification of Fourth Embodiment

Figure 25:
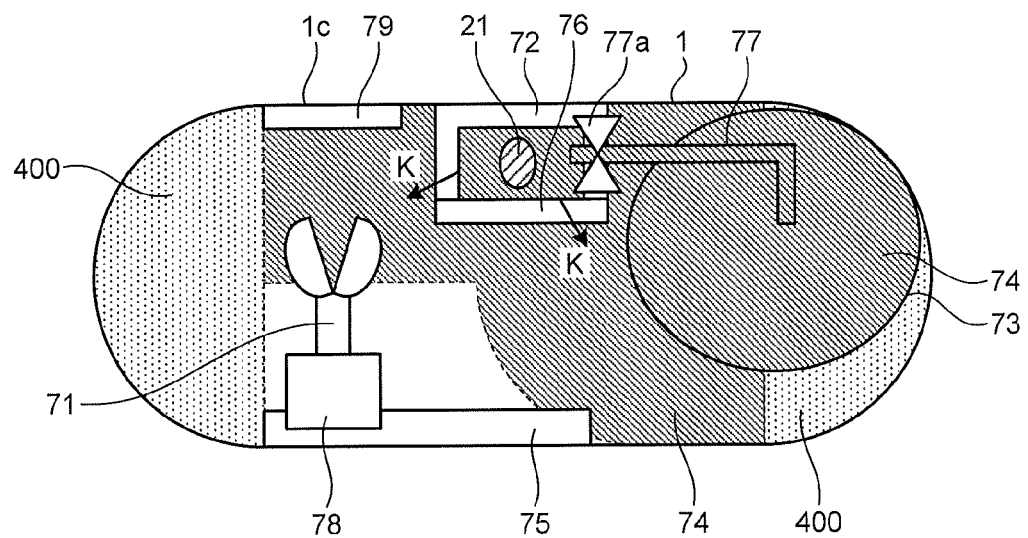
FIG. 25 is a schematic diagram illustrating the configuration of a capsule medical apparatus according to a first modification of the fourth embodiment of the present invention.

In the following, a first modification of the fourth embodiment of the present invention will be described. In the first modification of the fourth embodiment, the absorbers 400 not only absorb any leaked fixative solution but also swell by themselves, as illustrated in FIG. 25. The other configurations of the first modification of the fourth embodiment can be, for example, the same as those in the fourth embodiment.

In such a case, because the swelled absorbers 400 obstruct the opening/closing operation of the opening/closing portion 76 of the storage 72 and the opening/closing portion 79 of the capsule-shaped casing 1, the fixative solution 74 can be reliably prevented from leaking outside of the capsule-shaped casing 1. In FIG. 25, the leakage direction in a case where the fixative solution 74 is assumed to be leaked from the storage 72 is indicated, in outline, by the arrow K.

Second Modification of Fourth Embodiment

Figure 26:
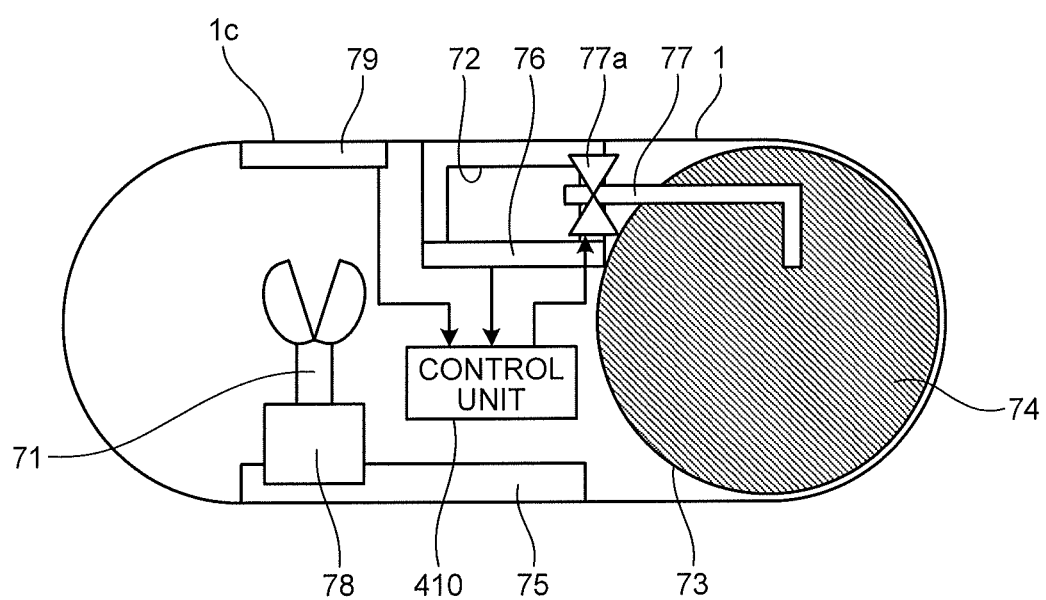
FIG. 26 is a schematic diagram illustrating the configuration of a capsule medical apparatus according to a second modification of the fourth embodiment of the present invention.

In the following, a second modification of the fourth embodiment of the present invention will be described. In the second modification of the fourth embodiment, as illustrated in FIG. 26, a control unit 410 detects the opening/closing operation of the opening/closing portion 79, which is an outer opening/closing means, and the opening/closing portion 76, which is a storage opening/closing means. When the opening/closing portions 79 and 76 are closed, the fixative solution 74 is supplied to the storage 72 by opening the valve 77a. The other configurations of the second modification of the fourth embodiment can be, for example, the same as those in the sixth modification of the first embodiment.

In this case, when the opening/closing portions 79 and 76 are closed, the control unit 410, by closing the valve 77a, does not perform the operation for supplying the fixative solution 74. Accordingly, even if the fixative solution 74 leaks, it is possible to prevent the fixative solution 74 from leaking outside the capsule-shaped casing 1.

Fifth Embodiment

In the following, a fifth embodiment of the present invention will be described. In the first to fourth embodiments described above, the in-vivo tissue 21 is collected using the forceps or the rotary blade. However, in the fifth embodiment, the in-vivo tissue 21 is collected using a needle that protrudes/retracts. The other configurations of the fifth embodiment can be, for example, the same as those in the first to fourth embodiments.

Figure 27A:
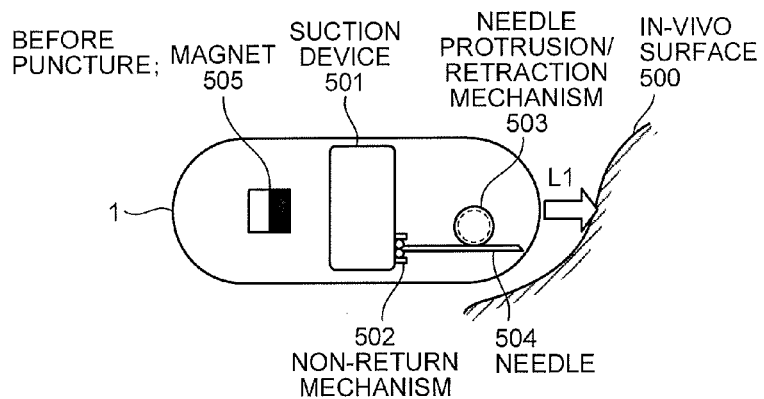
FIG. 27A is a schematic diagram illustrating the configuration and the operation of an in-vivo tissue collecting mechanism of a capsule medical apparatus according to a fifth embodiment of the present invention.

FIGS. 27A to 27D are schematic diagrams illustrating the configuration and the operation of an in-vivo tissue collecting mechanism of a capsule medical apparatus according to a fifth embodiment of the present invention. As illustrated in FIG. 27A, the in-vivo tissue collecting mechanism includes a suction device 501 that sucks in in-vivo tissue; a needle 504; a needle protrusion/retraction mechanism 503 that protrudes/retracts the needle 504; and a non-return mechanism 502 that allows the proximal end portion of the needle 504 to abut against and be inserted into the suction device 501 with a non-return function. In the capsule-shaped casing 1, a magnet 505 that functions as a magnetic material is arranged in such a manner that the magnetization direction corresponds to the longitudinal direction of the capsule-shaped casing 1.

When desired in-vivo tissue is collected and stored using the in-vivo tissue collecting mechanism, first, the capsule medical apparatus is moved by generating, in the magnet 505, a magnetic attracting force using an external magnetic field, and, as illustrated in FIG. 27A, the distal end of the needle 504 is brought closer to the in-vivo tissue that is to be collected. In FIG. 27A, the moving direction of the capsule medical apparatus is indicated by the arrow L1.

Figure 27B:
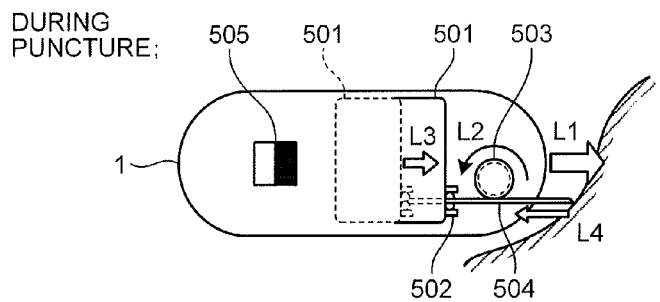
FIG. 27B is another schematic diagram illustrating the configuration and the operation of the in-vivo tissue collecting mechanism of the capsule medical apparatus according to the fifth embodiment of the present invention.
Figure 27C:
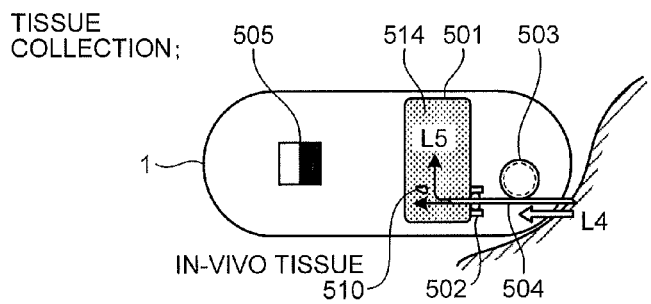
FIG. 27C is another schematic diagram illustrating the configuration and the operation of the in-vivo tissue collecting mechanism of the capsule medical apparatus according to the fifth embodiment of the present invention.

Then, as illustrated in FIG. 27B, by operating the needle protrusion/retraction mechanism 503, the needle 504 is made to protrude into an in-vivo surface 500 side so that the needle 504 is stuck into the in-vivo surface 500. In this case, the suction device 501 and the non-return mechanism 502 are made to move in the same direction in which the needle 504 moves. In FIG. 27B, the rotation direction of the needle protrusion/retraction mechanism 503 is indicated by the arrow L2, and the moving direction of the suction device 501 is indicated by the arrow L3. Furthermore, when the needle 504 moves on the in-vivo surface 500 side, the proximal end of the needle 504 abuts against the non-return mechanism 502. If the distal end of the needle 504 abuts against the in-vivo surface 500, the needle 504 breaks through the non-return mechanism 502 due to the reaction force of the needle 504, as illustrated in FIG. 27C. In FIGS. 27B and 27C, the reaction force direction is indicated by the arrow L4. Thereafter, the suction device 501 sucks in-vivo tissue 510 through the needle 504 and stores the in-vivo tissue 510. Furthermore, a fixative solution 514 is supplied from a liquid storage (not shown) to the suction device 501. In this case, the suction device 501 functions as a storage. In FIG. 27C, the moving direction of the in-vivo tissue 510 that has been sucked is indicated, in outline, by the arrow L5.

Figure 27D:
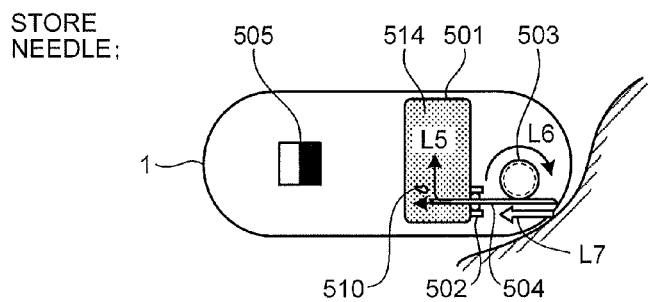
FIG. 27D is another schematic diagram illustrating the configuration and the operation of the in-vivo tissue collecting mechanism of the capsule medical apparatus according to the fifth embodiment of the present invention.

Then, as illustrated in FIG. 27D, by rotating the needle protrusion/retraction mechanism 503 in reverse, the needle 504 is retracted to the suction device 501 side, is pulled out from the in-vivo surface 500, and is stored in the capsule-shaped casing 1. When the needle 504 is pulled out, the needle 504 is further inserted into the suction device 501. In FIG. 27D, the rotation direction of the needle protrusion/retraction mechanism 503 is indicated by the arrow L6, and the pulling-out direction of the needle 504 is indicated by the arrow L7.

Figure 28:
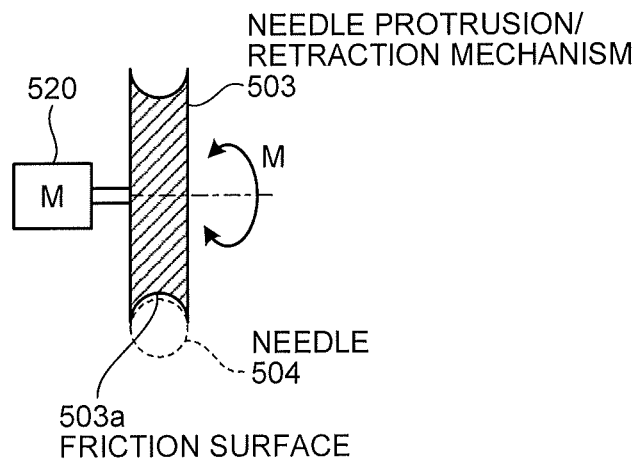
FIG. 28 is a schematic diagram illustrating the configuration of the needle protrusion/retraction mechanism illustrated in FIG. 27A.
Figure 29A:
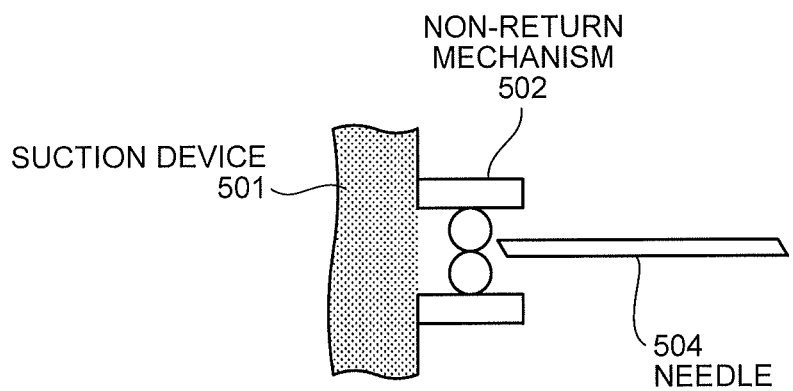
FIG. 29A is a schematic diagram illustrating a state in which the non-return mechanism illustrated in FIG. 27A is closed.
Figure 29B:
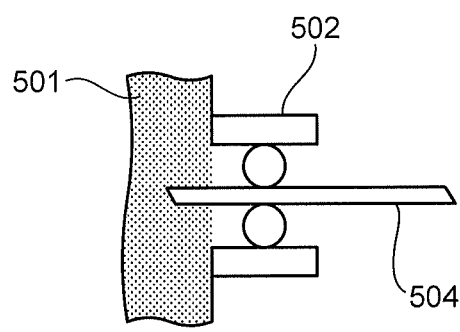
FIG. 29B is a schematic diagram illustrating a state in which the non-return mechanism illustrated in FIG. 27A is open.

Furthermore, as illustrated in FIG. 28, the needle protrusion/retraction mechanism 503 is rotated by a motor 520. A friction surface 503a is formed on the outer circumferential surface with which the needle 504 contacts. In FIG. 28, the rotation direction of the needle protrusion/retraction mechanism 503 is indicated by the arrow M. Furthermore, the interior of the suction device 501 is maintained in a vacuum or in a low pressure state, where the suctioning operation using the needle 504 can be performed. Here, as illustrated in FIG. 29A, when the needle 504 does not have a reaction force applied by the in-vivo surface 500, the non-return mechanism 502 is closed. As illustrated in FIG. 29B, when the needle 504 has a reaction force applied by the in-vivo surface 500, the non-return mechanism 502 is opened. As a result, the distal end of the needle 504 is inserted into the suction device 501. Here, as described above, because the interior of the suction device 501 is in a vacuum or in a low pressure state, the in-vivo tissue or the fixative solution that has been sucked is prevented from leaking outside the suction device 501.

In the fifth embodiment, in-vivo tissue is collected by puncturing the needle 504 into the in-vivo tissue and sucking the in-vivo tissue through the needle 504. Accordingly, the collecting operation is not prevented by air or body fluid near the in-vivo surface, thus reliably collecting the in-vivo tissue.

Figure 30A:
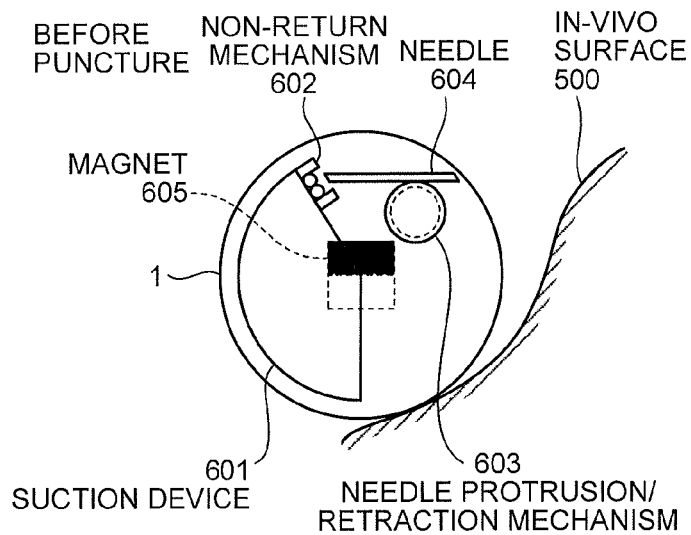
FIG. 30A is a schematic diagram explaining a collecting-and-storing process performed on in-vivo tissue by, from among the capsule medical apparatuses of the present invention, a capsule medical apparatus that can rotate by itself.
Figure 30B:
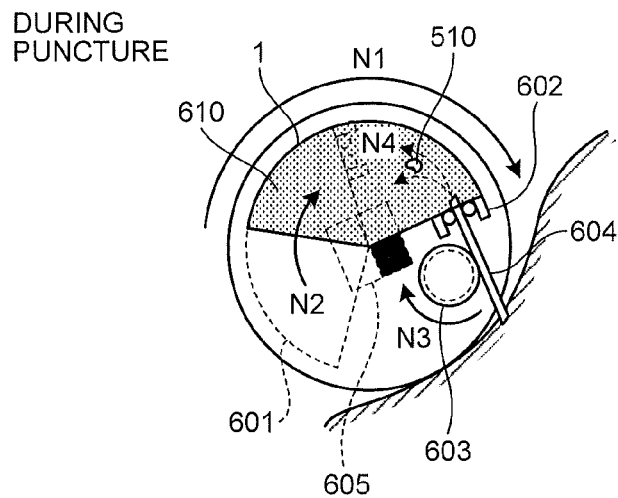
FIG. 30B is another schematic diagram explaining the collecting-and-storing process performed on the in-vivo tissue by, from among the capsule medical apparatuses of the present invention, a capsule medical apparatus that can rotate by itself.
Figure 30C:
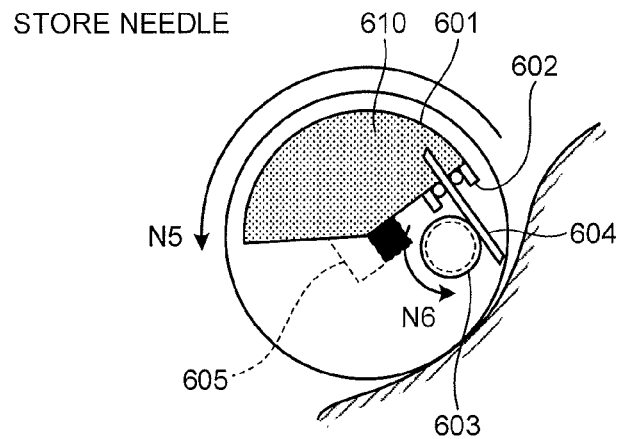
FIG. 30C is another schematic diagram explaining the collecting-and-storing process performed on the in-vivo tissue by, from among the capsule medical apparatuses of the present invention, a capsule medical apparatus that can rotate by itself.

Furthermore, as illustrated in FIG. 30A, a suction device 601, a non-return mechanism 602, a needle 604, and a needle protrusion/retraction mechanism 603 are arranged in this order in the circumferential direction. A magnet 605 can be arranged in the capsule-shaped casing 1 such that the magnetization direction of the magnet 605 corresponds to the radial direction of the capsule-shaped casing 1. When in-vivo tissue is collected, it is possible to collect the in-vivo tissue by bringing the capsule-shaped casing 1 closer to the in-vivo surface 500; by rotating the needle protrusion/retraction mechanism 603 to protrude the needle 604 corresponding to the needle 504, as illustrated in FIG. 30B; by rotating, using a rotating field, the capsule-shaped casing 1 in the circumferential direction to puncture the needle 604 into the in-vivo surface 500; and then, as illustrated in FIG. 30C, by sucking up the in-vivo tissue 510 using the suction device 601. In this case, it is preferable to generate a torque by rotating the suction device 601 and the non-return mechanism 602 together with the capsule-shaped casing 1. For example, after the in-vivo tissue 510 is collected, the needle 504 is pulled out from the in-vivo surface 500 by rotating the capsule-shaped casing 1 in reverse using a rotating field. Then the needle 604 can be stored in the capsule-shaped casing 1 by rotating the needle protrusion/retraction mechanism 603 in reverse.

In FIG. 30B, the rotation direction of the capsule-shaped casing 1 is indicated by the arrow N1, and the rotation direction of the suction device 601 and the non-return mechanism 602 is indicated by the arrow N2. Furthermore, the rotation direction of the needle protrusion/retraction mechanism 603 is indicated by the arrow N3, and the moving direction of the in-vivo tissue 510 that has been sucked is indicated, in outline, by the dashed lined arrow N4. In FIG. 30C, the reverse rotation direction of the capsule-shaped casing 1 is indicated by the arrow N5, and the reverse rotation direction of the needle protrusion/retraction mechanism 603 is indicated by the arrow N6.

Figure 31A:
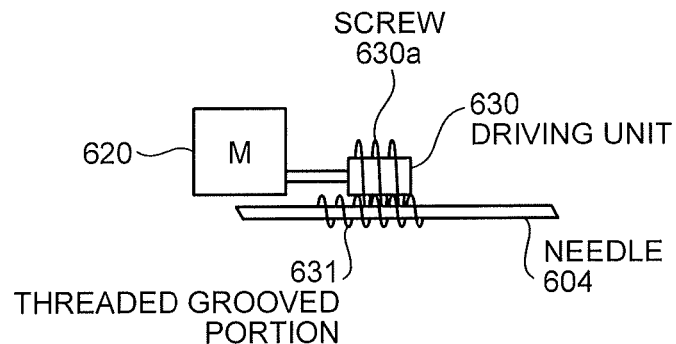
FIG. 31A a schematic diagram illustrating a modification of a needle protrusion/retraction mechanism of the capsule medical apparatus according to the fifth embodiment of the present invention.
Figure 31B:
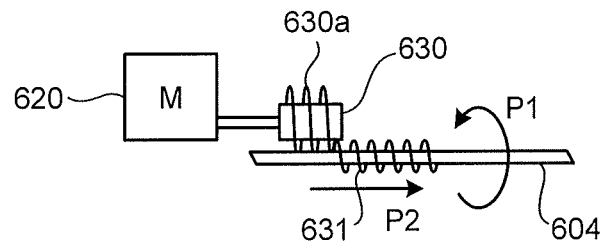
FIG. 31B is a schematic diagram illustrating the operation of the needle protrusion/retraction mechanism illustrated in FIG. 31A.
Figure 31C:
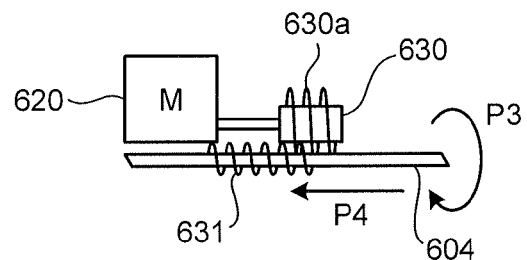
FIG. 31C is a schematic diagram illustrating another operation of the needle protrusion/retraction mechanism illustrated in FIG. 31A.

Furthermore, the configuration of the needle protrusion/retraction mechanism 503 is not limited to the configuration illustrated in FIG. 28. As illustrated in FIGS. 31A to 31C, the needle 604 can be linearly moved in the axis direction through a threaded grooved portion 631 by engaging a screw 630a that is arranged on the outer circumferential surface of the axis of a driving unit 630 with the threaded grooved portion 631 that is arranged on the outer circumferential surface of the axis of the needle 604 and by rotating the screw 630a of the driving unit 630 using the rotational movement of a motor 620. In FIG. 31B, the rotation direction of the screw 630a is indicated by the arrow P1, and the moving direction of the needle 604 is indicated by the arrow P2. Furthermore, in FIG. 31C, the rotation direction of the screw 630a is indicated by the arrow P3, and the moving direction of the needle 604 is indicated by the arrow P4.

Figure 32:
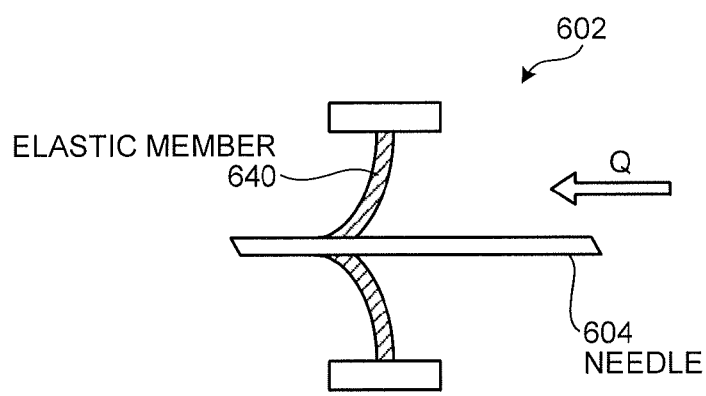
FIG. 32 is a schematic diagram illustrating a modification of a non-return mechanism of the capsule medical apparatus according to the fifth embodiment of the present invention.

Furthermore, as illustrated in FIG. 32, the non-return mechanism 602 can be implemented by using an elastic member 640 without using a roller. FIG. 32 is a schematic diagram illustrating the state of the elastic member 640 when the needle 604 moves in the direction indicated by the arrow Q.

Figure 33:
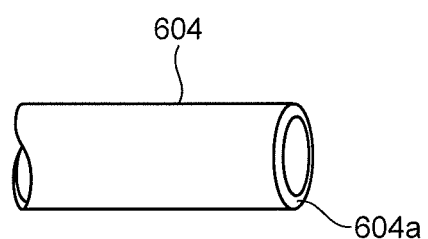
FIG. 33 is a schematic diagram illustrating the shape of the distal end of a needle in the capsule medical apparatus according to the fifth embodiment of the present invention.

Furthermore, as illustrated in FIG. 33, a distal end 604a of the needle 604 can be made flat so that a contact surface with in-vivo tissue becomes widened, thus easily sucking up the in-vivo tissue.

Figure 34:
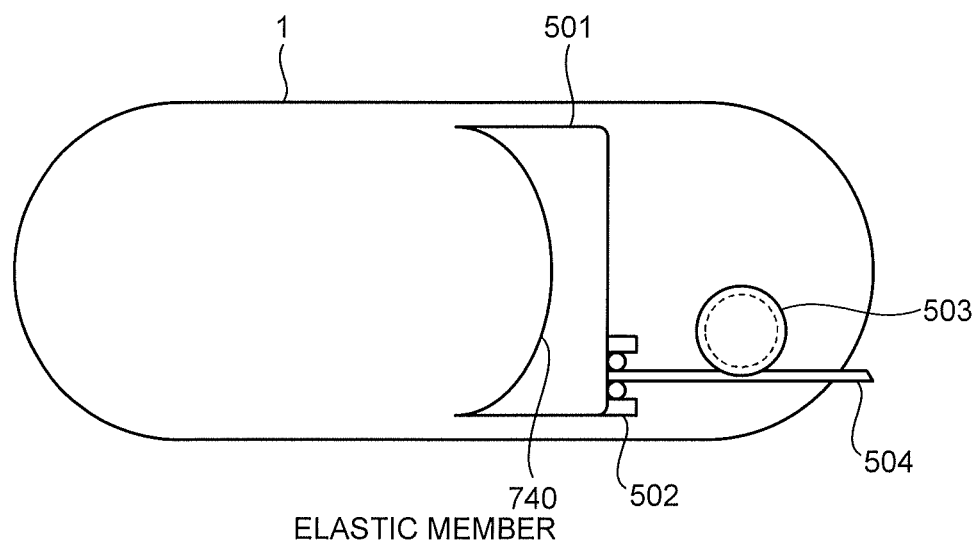
FIG. 34 is a schematic diagram illustrating an example of a suction device in the capsule medical apparatus according to the fifth embodiment of the present invention.

Furthermore, as illustrated in FIG. 34, a wall surface at the opposite side from the surface on which the non-return mechanism 502 of the suction device 501 is arranged can be formed of an elastic member 740, and an internal space is made to be in a negative pressure state using the restoring force in the external direction due to the elastic member 740, whereby in-vivo tissue can be sucked through the needle 504 using this pressure.

Figure 35:
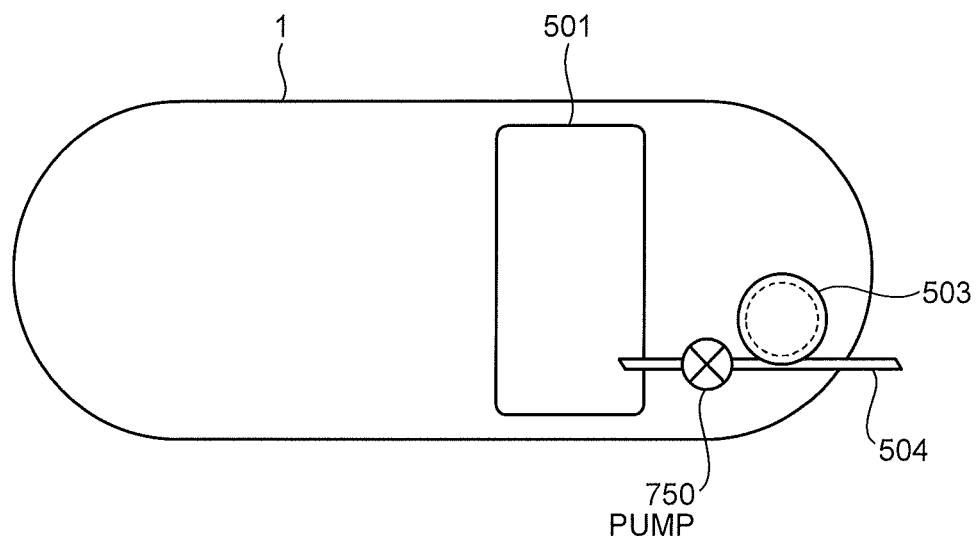
FIG. 35 is a schematic diagram illustrating another example of the suction device in the capsule medical apparatus according to the fifth embodiment of the present invention.

Furthermore, as illustrated in FIG. 35, instead of arranging the non-return mechanism, a pump 750 for sucking up in-vivo tissue can be directly attached to the needle 504 without making the suction device 501 be in a negative pressure state.

Figure 36:
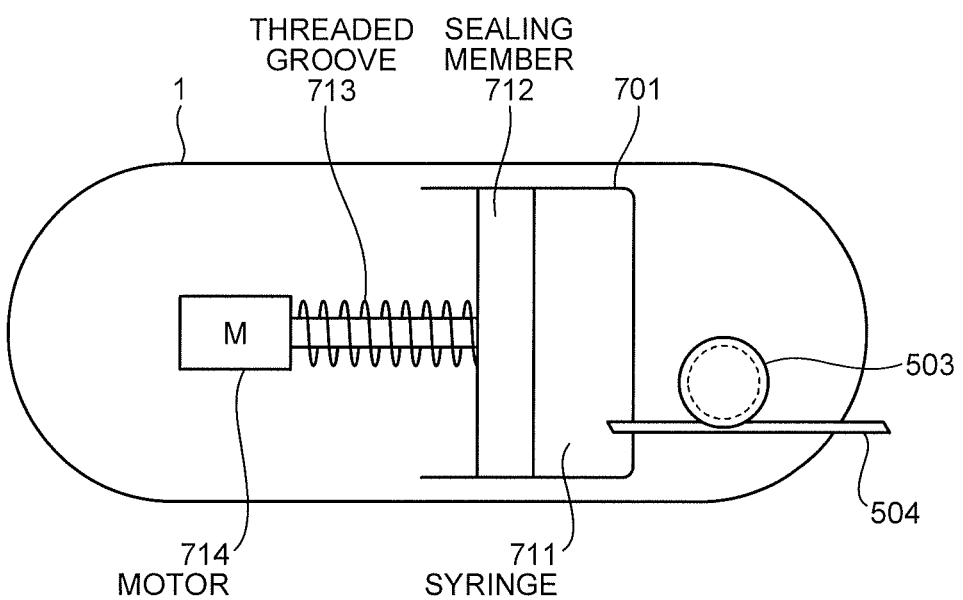
FIG. 36 is a schematic diagram illustrating another example of the suction device in the capsule medical apparatus according to the fifth embodiment of the present invention.

Furthermore, as illustrated in FIG. 36, in-vivo tissue can be sucked through the needle 504 by arranging a sealing member 712 that is arranged on a side opposite to a position where the needle 504 of a suction device 701 is arranged and that forms a sealed space in a syringe 711 by entering the syringe 711; arranging a ball screw that includes a threaded groove 713 that moves the sealing member 712 in the direction in which the sealed space formed by the sealing member 712 is widened; and arranging a motor 714 that rotates the ball screw, thereby widening the sealed space due to the rotation of the ball screw.

Sixth Embodiment

In the following, a sixth embodiment of the present invention will be described. In the sixth embodiment, an attempt is made to cauterize a wounded portion generated when in-vivo tissue is collected. The other configurations except for a cauterization process in the sixth embodiment can be, for example, the same as those in the first to fifth embodiments or modifications thereof.

Figure 37A:
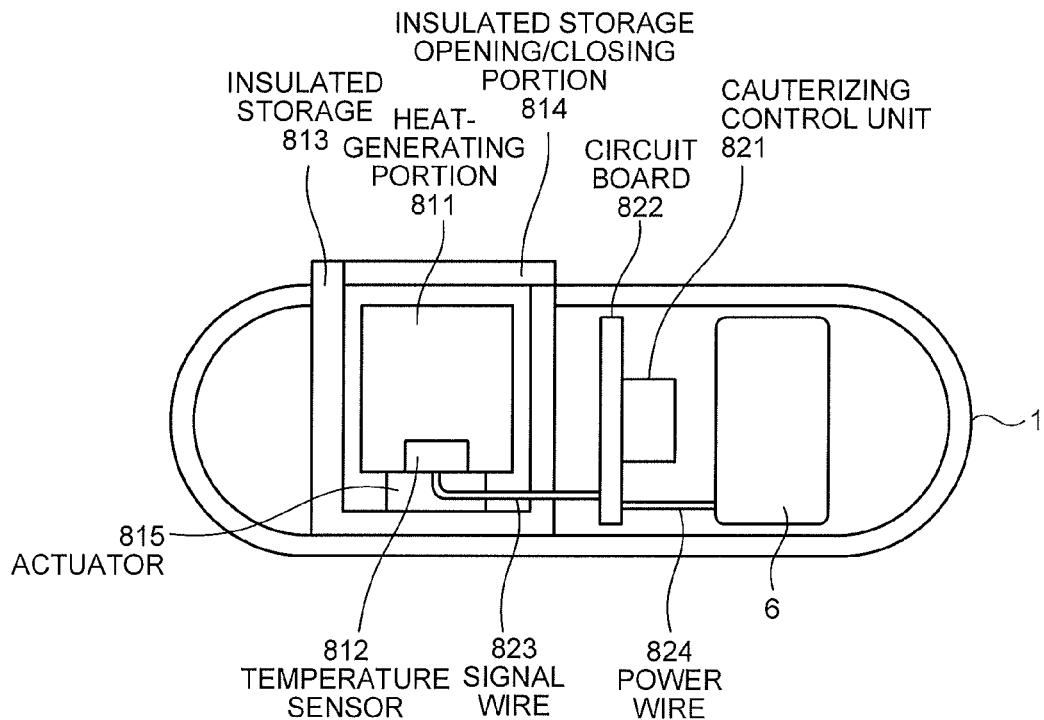
FIG. 37A is a schematic diagram illustrating the configuration and the operation of a cauterizing mechanism of a capsule medical apparatus according to a sixth embodiment of the present invention.
Figure 37B:
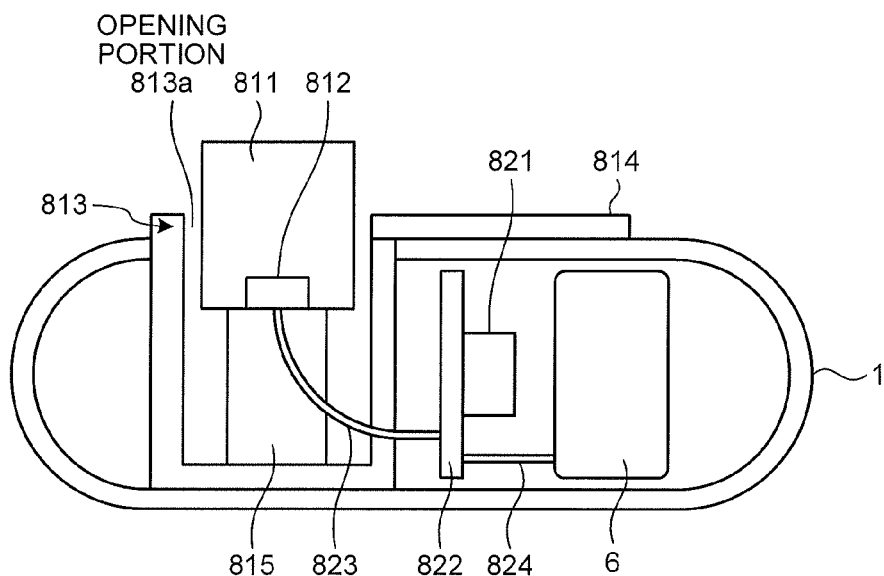
FIG. 37B is another schematic diagram illustrating the configuration and the operation of the cauterizing mechanism of the capsule medical apparatus according to the sixth embodiment of the present invention.

FIGS. 37A and 37B are schematic diagrams illustrating the configuration and the operation of a cauterizing mechanism of a capsule medical apparatus according to a sixth embodiment of the present invention. As illustrated in FIGS. 37A and 37B, the capsule medical apparatus has a heat-generating portion 811, functioning as a cauterizing means, that cauterizes in-vivo tissue by protruding outside the capsule-shaped casing 1 and a temperature sensor 812 that is arranged near the heat-generating portion 811 and detects the temperature thereof. Furthermore, the capsule medical apparatus has an insulated storage 813, functioning as an insulated storing means, that is formed of a low heat conducting material and that accommodates the heat-generating portion 811 and the temperature sensor 812; an insulated storage opening/closing portion 814, functioning as an insulation opening/closing means, that is formed of a low heat conducting material and that opens/closes the insulated storage 813; and an actuator 815 that protrudes/retracts the heat-generating portion 811 from the insulated storage 813. Furthermore, the capsule medical apparatus has a circuit board 822 on which a cauterizing control unit 821 is mounted; a signal wire 823 that connects the cauterizing control unit 821, the heat-generating portion 811, the temperature sensor 812, and the actuator 815; and a power wire 824 that connects the circuit board 822 and the power supply 6.

The cauterizing control unit 821 controls the electrical power supplied from the power supply 6 such that the heat-generating portion 811 generates heat in accordance with the supplied amount of electrical power. The cauterizing control unit 821 observes the temperature detected by the temperature sensor 812 and controls the supplied amount of electrical power from the power supply 6 to the heat-generating portion 811 such that the temperature of the heat-generating portion 811 becomes a predetermined temperature.

The insulated storage 813 is a box having a single opening portion 813a and is formed of a solid low heat conducting material whose heat conductivity is low, such as glass, ceramic, or a synthetic resin. The insulated storage 813 is accommodated in the capsule-shaped casing 1 with the opening portion 813a being protruded from the capsule-shaped casing 1 outward in the radial direction of the capsule-shaped casing 1. In a similar manner as with the insulated storage 813, the insulated storage opening/closing portion 814 is formed of a solid low heat conducting material whose heat conductivity is low. Under the control of the cauterizing control unit 821, the insulated storage opening/closing portion 814 opens/closes the opening portion 813a by shifting in the longitudinal direction of the capsule-shaped casing 1. The actuator 815 is arranged in the insulated storage 813 such that the actuator 815 and the opening portion 813a are opposed to each other across the heat-generating portion 811 and the actuator 815 expands/contracts, under the control of the cauterizing control unit 821, in the radial direction of the capsule-shaped casing 1.

When in-vivo tissue is cauterized using the heat-generating portion 811, as illustrated in FIG. 37B, the insulated storage opening/closing portion 814 shifts in a predetermined direction to expose the opening portion 813a, and, in this state, the actuator 815 extends in the radial direction of the capsule-shaped casing 1, so that the heat-generating portion 811 protrudes, from the opening portion 813a, outside of the insulated storage 813. In the following, a cauterization process performed by the capsule medical apparatus on in-vivo tissue will be specifically described with reference to FIGS. 38A and 38B.

Figure 38A:
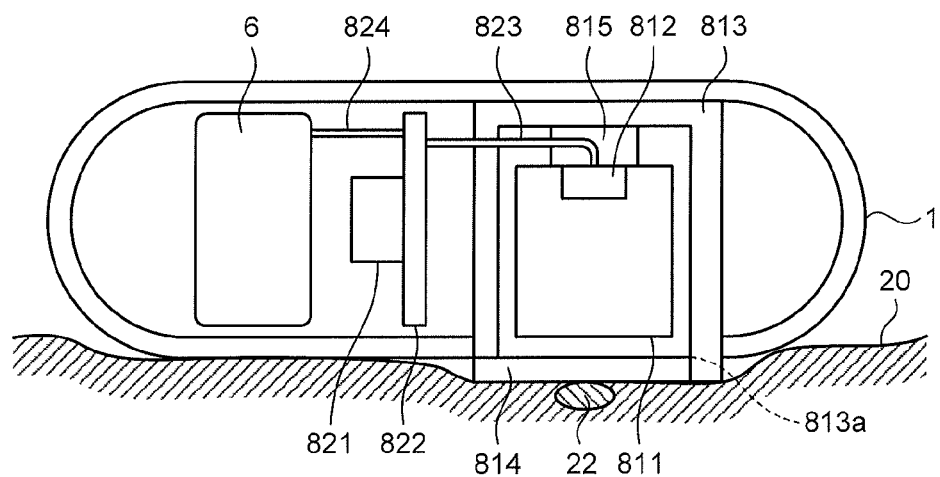
FIG. 38A is a schematic diagram illustrating a part of a procedure of a cauterization process performed by the capsule medical apparatus illustrated in FIG. 37.
Figure 38B:
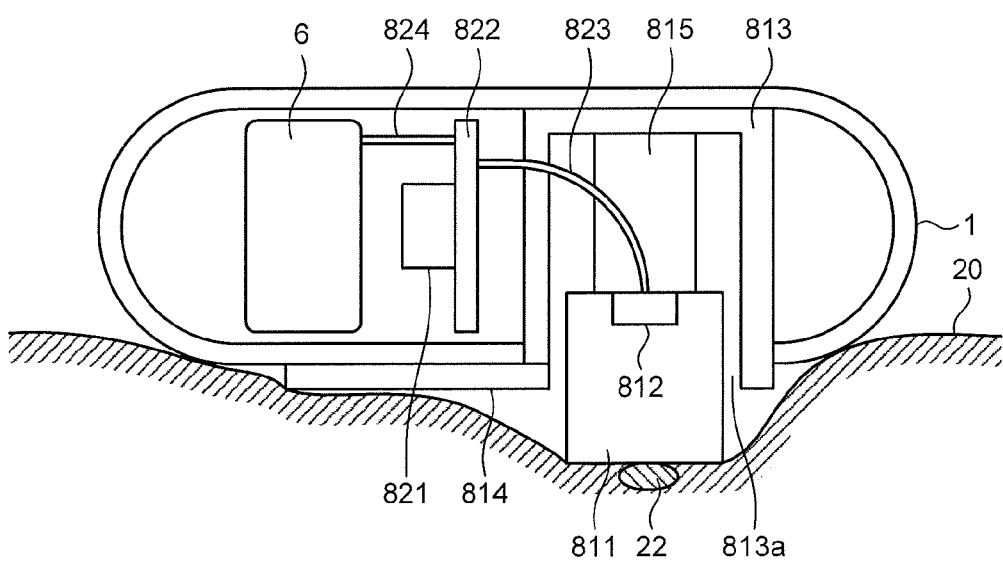
FIG. 38B is a schematic diagram illustrating another part of the procedure of the cauterization process performed by the capsule medical apparatus illustrated in FIG. 37.

FIGS. 38A and 38B are schematic diagrams illustrating the procedure of the cauterization process performed by the capsule medical apparatus illustrated in FIGS. 37A and 37B. When the cauterization process is performed by the capsule medical apparatus on in-vivo tissue, first, as illustrated in FIG. 38A, the in-vivo tissue to be cauterized, e.g., a wounded portion 22 generated in in-vivo tissue 20 due to tissue collection, is brought into contact with the insulated storage opening/closing portion 814. At this time, the opening portion 813a is closed by the insulated storage opening/closing portion 814. Furthermore, under the control of the cauterizing control unit 821, the heat-generating portion 811 is heated to a predetermined temperature by supplying electrical power from the power supply 6 to the heat-generating portion 811.

Then, as illustrated in FIG. 38B, under the control of the cauterizing control unit 821, the opening portion 813a is opened by shifting the insulated storage opening/closing portion 814 to a predetermined direction; thereafter, the actuator 815 is extended in the radial direction of the capsule-shaped casing 1 so as to protrude the heat-generating portion 811 outside the insulated storage 813 from the opening portion 813a; and the heat-generating portion 811 is pressed against the wounded portion 22. By doing so, the cauterization process is performed on the wounded portion 22 by the heat-generating portion 811. The cauterization process is performed, under the control of the cauterizing control unit 821, for example, for a predetermined period of time that is set in advance.

When the heat-generating portion 811 completes the cauterization process subjected to the wounded portion 22, under the control of the cauterizing control unit 821, the heat-generating portion 811 is accommodated in the insulated storage 813 by contracting the actuator 815 in the radial direction of the capsule-shaped casing 1 and then the opening portion 813a is closed by shifting the insulated storage opening/closing portion 814 in a predetermined direction.

In the sixth embodiment, because the cauterization process can be performed on the wounded portion 22 following the collection of in-vivo tissue, bleeding from the wounded portion 22 can be stopped by the cauterization process. As a result, it is possible to prevent the in-vivo tissue 20 from being infected, through the wounded portion 22, with bacteria or a virus. Accordingly, in-vivo tissue can be collected more safely.

Furthermore, because the heat-generating portion 811 is heated in the insulated storage 813, heat generated in the heat-generating portion 811 is hard to dissipate outside the insulated storage 813; therefore, the heat-generating portion 811 can be heated to a desired temperature in a short period of time with a relative small amount of electrical power. Accordingly, for the power supply 6, it is possible to use a relatively small-size power supply whose output power is relatively low. This enables the increase in size of the capsule medical apparatus due to the addition of the cauterization function thereto to be reduced. Furthermore, because the amount of heat dissipated outside the insulated storage 813 can be reduced, it is possible to reduce damage, caused by heat, to other components accommodated in the capsule-shaped casing 1 or the capsule-shaped casing 1 itself.

First Modification of Sixth Embodiment

In the following, a first modification of the sixth embodiment of the present invention will be described. In the sixth embodiment described above, the insulated storage and the insulated storage opening/closing portion are each formed of solid low heat conducting material. However, in the first modification of the sixth embodiment, at least one of the insulated storage and the insulated storage opening/closing portion is configured to have an insulated double layer structure, thereby attempting to increase the insulation performance thereof. The other configurations of the first modification of the sixth embodiment, except for the insulated double layer structure used for the insulated storage and the insulated storage opening/closing portion, can be, for example, the same as those in the sixth embodiment.

Figure 39:
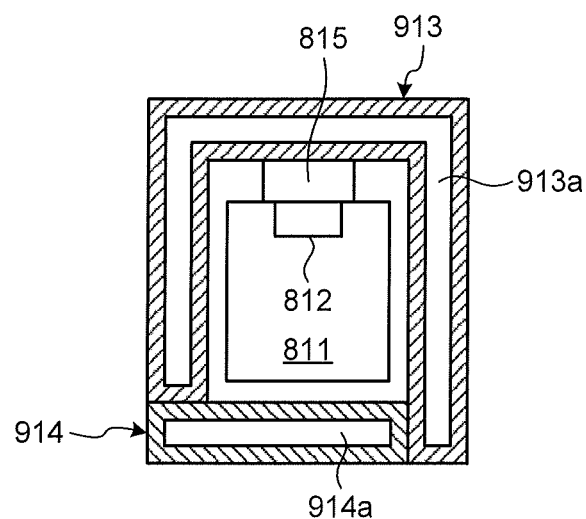
FIG. 39 is a schematic diagram illustrating the cross-sectional structure of an insulated storage and an insulated storage opening/closing portion of a capsule medical apparatus according to a first modification of the sixth embodiment of the present invention.

FIG. 39 is a schematic diagram illustrating the cross-sectional structure of the insulated storage and the insulated storage opening/closing portion of a capsule medical apparatus according to the first modification of the sixth embodiment of the present invention. As illustrated in FIG. 39, an insulated storage 913 in the capsule medical apparatus is a box shaped hollow member made of, for example, glass having a low heat conductivity. An insulated storage opening/closing portion 914 is configured as a plate shaped hollow member made of, for example, glass having a low heat conductivity. A gap 913a, which is a hollow member and forms the insulated storage 913, and a gap 914a, which is a hollow member and forms the insulated storage opening/closing portion 914 are filled with a gas, such as air, having low heat conductivity. At least one of the gap 913a and 914b can be, of course, a vacuum. The heat-generating portion 811, the temperature sensor 812, and the actuator 815 are accommodated in the insulated storage 913.

In the first modification of the sixth embodiment, because the insulated storage 913 and the insulated storage opening/closing portion 914 each have an insulated double layer structure, when compared with the capsule medical apparatus in the sixth embodiment, it is possible to reduce the amount of heat dissipated outside the insulated storage 913. Therefore, the heat-generating portion 811 can be heated to a desired temperature in a short period of time with a small amount electrical power. Accordingly, for the power supply 6, it is possible to use a small-size power supply having lower output power. This enables the increase in size of the capsule medical apparatus due to addition of the cauterization function thereto to be further reduced. Furthermore, because the amount of heat dissipated outside the insulated storage 913 can be reduced, it is possible to further reduce damage, caused by heat, to other components accommodated in the capsule-shaped casing or the capsule-shaped casing itself.

Furthermore, in the drawings corresponding to the embodiments described above, drawings of, for example, the imaging unit, the illumination unit, the wireless unit, the control unit, the power supply, and the magnet are omitted where appropriate. Furthermore, hatching of cross sections is also omitted where appropriate.

With the configuration used for performing the cauterization process described in the sixth embodiment or the first modification thereof, it is also possible to use a capsule medical apparatus that does not have a function of collecting in-vivo tissue. Furthermore, the cauterization process can be performed in order to, in addition to stopping bleeding, necrose diseased tissue.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical apparatus to be introduced into a subject, comprising:
    a tissue collecting unit that collects in-vivo tissue;
    a storage unit that stores therein the in-vivo tissue that is collected by the tissue collecting unit;
    a liquid storing unit that stores therein liquid for suppressing autolysis of in-vivo tissue;
    a liquid supplying unit that supplies the liquid in the liquid storing unit to the storage unit;
    an outer opening/closing unit that opens and closes a part of an outer casing of the capsule medical apparatus; and
    a control unit that performs, in response to an instruction to start collecting the in-vivo tissue, a control in which the outer opening/closing unit is opened and the tissue collecting unit collects desired in-vivo tissue and stores the collected in-vivo tissue in the storage unit, then a control in which the outer opening/closing unit is closed, and a control in which the liquid supplying unit supplies the liquid to the storage unit and the storage unit is made to be in a liquid-tight state, wherein
    absorbers that obstruct, by swelling, an opening and closing operation of the outer opening/closing unit are arranged outside each of the storage unit and the liquid supplying unit.

2. The capsule medical apparatus according to claim 1, further comprising a storage opening/closing unit that opens and closes a part of the storing unit.

3. The capsule medical apparatus according to claim 1, wherein the liquid is a fixative solution.

4. The capsule medical apparatus according to claim 1, wherein the liquid is a refrigerant.

5. The capsule medical apparatus according to claim 4, wherein the storage unit is covered by a heat blocking member.

6. The capsule medical apparatus according to claim 4, wherein an exterior of the storage unit has a double layered structure, an inner wall of the storage unit is formed of a member having high heat conductivity, and an outer wall is formed of a heat blocking member.

7. The capsule medical apparatus according to claim 1, further comprising a cooling unit that is arranged inside the capsule medical apparatus and that cools inside the storage unit, wherein the liquid is an antifreeze solution.

8. The capsule medical apparatus according to claim 7, wherein the cooling unit cools inside the storage unit using vaporization heat obtained when a compressed fluid is vaporized.

9. The capsule medical apparatus according to claim 7, wherein the storage unit is covered by a heat blocking member.

10. The capsule medical apparatus according to claim 7, wherein an exterior of the storage unit has a double layered structure, an inner wall of the storage unit is formed of a member having high heat conductivity, and an outer wall is formed of a heat blocking member.

11. The capsule medical apparatus according to claim 1, further comprising a magnetic material that is arranged inside the capsule medical apparatus.

12. The capsule medical apparatus according to claim 1, further comprising:
    an imaging unit that captures images of the inside of the subject; and
    an illumination unit that illuminates the inside of the subject.

* * * * *